US012721686B2

(12) United States Patent
Xu et al.

(10) Patent No.: US 12,721,686 B2
(45) Date of Patent: Sep. 1, 2026

(54) CONTINUUM INSTRUMENT AND SURGICAL ROBOT

(71) Applicant: BEIJING SURGERII ROBOTICS COMPANY LIMITED, Beijing (CN)

(72) Inventors: Kai Xu, Beijing (CN); Xu Liu, Beijing (CN)

(73) Assignee: BEIJING SURGERII ROBOTICS COMPANY LIMITED, Beijing (CN)

(*) Notice: Subject to any disclaimer, the term of this patent is extended or adjusted under 35 U.S.C. 154(b) by 705 days.

(21) Appl. No.: 18/010,060

(22) PCT Filed: Mar. 16, 2021

(86) PCT No.: PCT/CN2021/080948

§ 371 (c)(1),
(2) Date: Dec. 13, 2022

(87) PCT Pub. No.: WO2022/001187

PCT Pub. Date: Jan. 6, 2022

(65) Prior Publication Data

US 2023/0225806 A1 Jul. 20, 2023

(30) Foreign Application Priority Data

Jun. 30, 2020 (CN) ......................... 202010617370.5
Jun. 30, 2020 (CN) ......................... 202010618750.0
Jun. 30, 2020 (CN) ......................... 202010623369.3

(51) Int. Cl.
*A61B 34/30* (2016.01)
*A61B 17/00* (2006.01)

(52) U.S. Cl.
CPC ...... *A61B 34/30* (2016.02); *A61B 2017/0069* (2013.01); *A61B 2034/301* (2016.02); *A61B 2034/304* (2016.02)

(58) Field of Classification Search
CPC ............ A61B 34/30; A61B 2017/0069; A61B 2034/301; A61B 2034/304; A61B 34/71
(Continued)

(56) References Cited

U.S. PATENT DOCUMENTS

2006/0199999 A1 9/2006 Ikeda et al.
2009/0283647 A1* 11/2009 Yasunaga ............... A61B 90/50 248/123.2
2015/0352728 A1* 12/2015 Wang ....................... B25J 18/06 74/490.04

FOREIGN PATENT DOCUMENTS

CN 103085083 A 5/2013
CN 103340731 A 10/2013
(Continued)

*Primary Examiner* — Carl H Layno
*Assistant Examiner* — Mary Grace Schlueter
(74) *Attorney, Agent, or Firm* — SZDC Law PC

(57) ABSTRACT

A continuum instrument includes: at least one proximal continuum, at least one distal continuum, a drive connection part, and a drive transmission mechanism. The drive connection part is connected to a proximal stop disk of the proximal continuum, and includes an input end located at a proximal side of the proximal stop disk. An output end of the drive transmission mechanism is connected to the input end of the drive connection part, and the output end is configured to drive the input end such that the proximal stop disk turns to drive the distal continuum to bend by means of proximal structural backbones of the proximal continuum and distal structural backbones of the distal continuum.

18 Claims, 19 Drawing Sheets

(58) Field of Classification Search
USPC .............................................................. 606/1
See application file for complete search history.

(56) References Cited

FOREIGN PATENT DOCUMENTS

| | | | | |
|---|---|---|---|---|
| CN | 103948435 | A | 7/2014 | |
| CN | 104758060 | A | 7/2015 | |
| CN | 106236270 | A | 12/2016 | |
| CN | 106308934 | A | 1/2017 | |
| CN | 106510848 | A | 3/2017 | |
| CN | 106562806 | A | 4/2017 | |
| CN | 109431602 | A | 3/2019 | |
| CN | 110037795 | A | 7/2019 | |
| CN | 110234293 | A | 9/2019 | |
| CN | 111317570 | A | 6/2020 | |
| EP | 3508136 | A1 | 7/2019 | |
| EP | 3508310 | A1 | 7/2019 | |
| EP | 3524201 | A1 | 8/2019 | |
| WO | WO-2010002544 | A1 * | 1/2010 | ............ A61B 1/005 |
| WO | 2018041201 | A1 | 3/2018 | |
| WO | 2018041211 | A1 | 3/2018 | |

* cited by examiner

CONTINUUM INSTRUMENT AND SURGICAL ROBOT

CROSS REFERENCE TO RELATED APPLICATIONS

The present application is the National Stage Application of PCT/CN2021/080948, filed on Mar. 16, 2021, which claims the right of priority of the Chinese patent application No. 2020106173705, filed on Jun. 30, 2020, and entitled "Surgical Tool Drive Transmission System Based on Planar Motion Mechanism, and Surgical Robot", the Chinese patent application No. 2020106233693, filed on Jun. 30, 2020, and entitled "Flexible Continuum Drive Transmission Mechanism, Surgical Tool Driving System, and Robot", and the Chinese patent application No. 2020106187500, filed on Jun. 30, 2020, and entitled "Surgical Tool Drive Transmission System, and Surgical Robot Including Same", which are incorporated herein by reference in their entirety.

TECHNICAL FIELD

The present disclosure relates to the field of medical instruments, and in particular to a continuum instrument and a surgical robot.

BACKGROUND ART

Minimally invasive procedures cause less injury to patients and faster postoperative recovery, and have been of great significance in surgery. In a minimally invasive procedure, surgical instruments, including surgical tools and visual lighting modules, all enter the human body through an incision or a natural orifice and then reach a surgical site to perform a surgical operation. In an existing surgical instrument, a distal structure is mainly composed of multiple rods hinged in series, and is driven by a pulling force from a steel wire rope so that the surgical instrument can bend at a hinged joint. Since the steel wire rope must be maintained in a continuous tension state by means of a pulley, this driving method can hardly achieve further miniaturization of the surgical instrument and further improvement of kinematic performance of the instrument.

In contrast to a traditional rigid kinematic chain which achieves a bending motion by means of mutual rotation at joints, a flexible continuum structure can achieve continuous bending deformation, and thus the flexible continuum structure is widely used in the research and development of medical instruments such as flexible manipulators, endoscopes and controllable catheters, and new-type special equipment such as industrial deep-cavity detection endoscopes and flexible mechanical arms.

Generally, in an existing continuum structure, a drive wire in the continuum structure is directly pushed and pulled by means of a drive mechanism so that the continuum structure can bend in any direction. However, with the stricter requirements for a continuum structure, such as high precision, fast response, high flexibility of bending, and good stability, the existing drive structures gradually no longer satisfy the above requirements. In addition, in the existing driving method, the motion is performed by means of directly pushing and pulling a drive wire, and thus when there is a large number of drive wires, the number of drive mechanisms will also increase accordingly, making the structure complex.

SUMMARY OF THE INVENTION

In some embodiments, the present disclosure provides a continuum instrument, comprising: at least one proximal continuum comprising a proximal stop disk and a plurality of proximal structural backbones, with proximal ends of the plurality of proximal structural backbones being fixedly connected to the proximal stop disk; at least one distal continuum comprising a distal stop disk and a plurality of distal structural backbones, with distal ends of the plurality of distal structural backbones being fixedly connected to the distal stop disk, and the plurality of distal structural backbones being fixedly connected to or integrally formed with the plurality of proximal structural backbones; and a drive connection part connected to the proximal stop disk, the drive connection part comprising an input end located at a proximal side of the proximal stop disk; and a drive transmission mechanism, having an output end connected to the input end of the drive connection part, the output end being configured to drive the input end such that the proximal stop disk turns to drive the distal continuum to bend by means of the proximal structural backbones and the distal structural backbones.

In some embodiments, the present disclosure provides a surgical robot, comprising at least one surgical trolley, at least one positioning arm, and at least one surgical instrument, wherein the at least one surgical instrument comprises at least one continuum instrument as described above and an end device disposed at a distal end of the continuum instrument; and the at least one positioning arm is movably disposed on the at least one surgical trolley, and at least one surgical instrument is disposed at a distal end of the at least one positioning arm.

BRIEF DESCRIPTION OF THE DRAWINGS

In order to explain the technical solutions in the embodiments of the present disclosure more clearly, the accompanying drawings used in the description of the embodiments will be briefly introduced below. Obviously, the accompanying drawings in the following description only show some of the embodiments of the present disclosure, and for those of ordinary skill in the art, other embodiments would also have been obtained from the contents of the embodiments of the present disclosure and these accompanying drawings without involving any inventive effort.

FIG. 2(*b*) shows a schematic structural diagram of a drive connection part according to some embodiments of the present disclosure;

FIG. 4(*b*) shows a schematic structural diagram of another drive connection part according to some embodiments of the present disclosure;

DETAILED DESCRIPTION OF THE EMBODIMENTS

In order to clarify the technical problem to be solved, the technical solutions used and the technical effects achieved in the present disclosure in a better way, the technical solutions of embodiments of the present disclosure will be described in further detail below in conjunction with the accompanying drawings. Obviously, the embodiments described are merely exemplary embodiments, rather than all the embodiments of the present disclosure.

In the description of the present disclosure, it should be noted that the orientation or position relationships indicated by the terms "center", "upper", "lower", "left", "right", "vertical", "horizontal", "inner", "outer", etc. are based on the orientation or position relationships shown in the accompanying drawings and are merely for ease of description of the present disclosure and simplification of the description, rather than indicating or implying that the devices or elements referred to must have a specific orientation or be constructed and operated in a specific orientation, and thus cannot be construed as limiting the present disclosure. Moreover, the terms "first" and "second" are merely used for the illustrative purpose, and should not be construed as indicating or implying the relative importance. In the description of the present disclosure, it should be noted that the terms "mounting", "connecting", "connection" and "coupling" should be appreciated in a generalized sense, unless otherwise explicitly specified and defined, and for example, may be a fixed connection or a detachable connection, may be a mechanical connection or an electrical connection, may be a direct connection or an indirect connection via an intermediate medium, and may be communication between the interiors of two components. For those of ordinary skill in the art, the specific meanings of the terms mentioned above in the present disclosure should be construed according to specific circumstances. The present disclosure defines the end close to an operator (e.g., a surgeon) as a proximal end or portion or a rear end or portion, and the end close to a patient undergoing surgery as a distal end or portion or a front end or portion. Those skilled in the art will appreciate that the embodiments of the present disclosure can be used in medical instruments or surgical robots, and can also be used in other non-medical devices.

Figure 1:
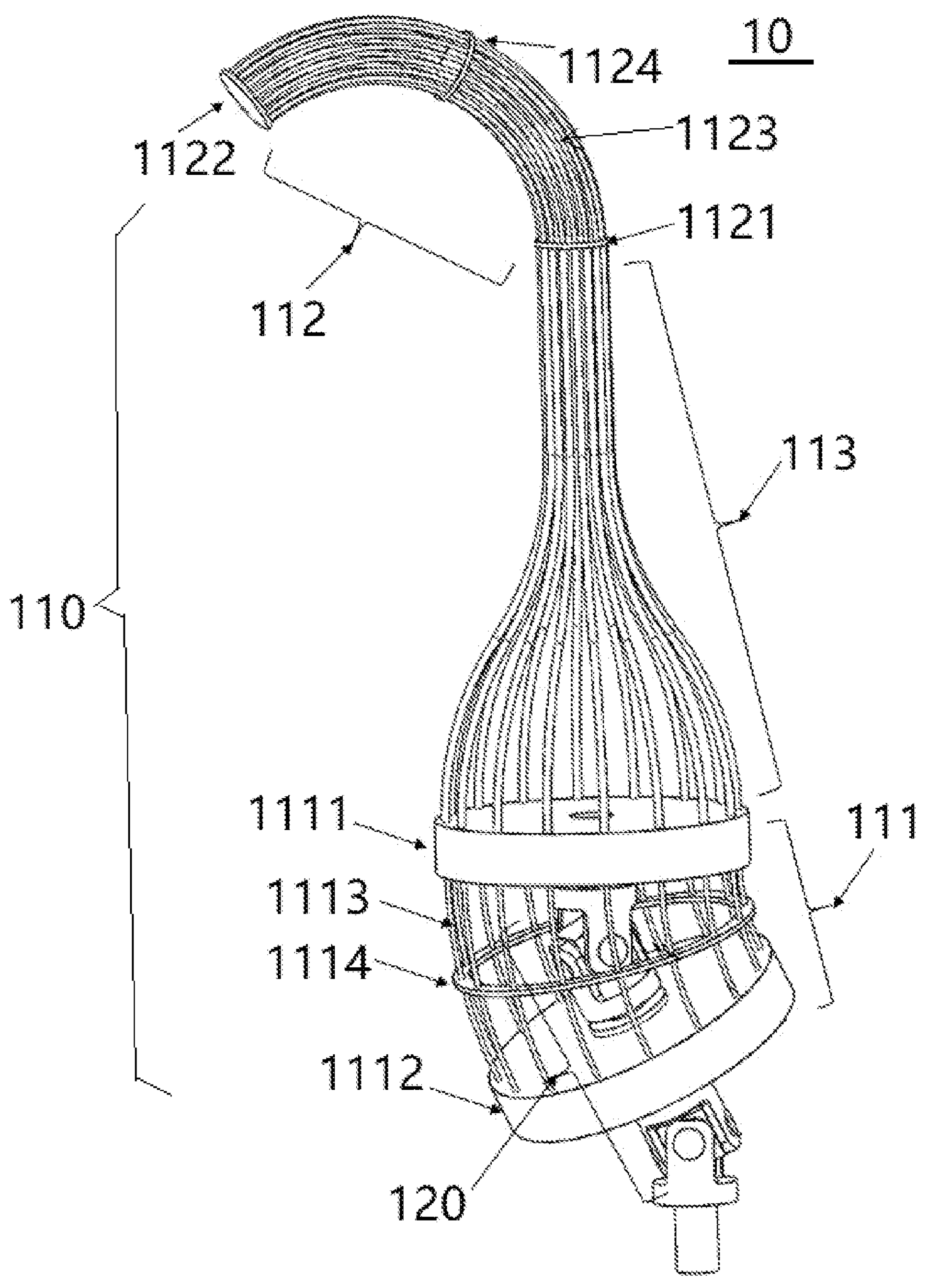
FIG. 1 shows a schematic structural diagram of a continuum instrument according to some embodiments of the present disclosure.

FIG. 1 shows a continuum instrument 10 according to some embodiments of the present disclosure. As shown in FIG. 1, the continuum instrument 10 may include a flexible continuum structure 110 and a drive connection part 120. The flexible continuum structure 110 may include at least one proximal continuum 111 located at a proximal end, and at least one distal continuum 112 located at a distal end. The proximal continuum 111 may include a proximal base disk 1111, a proximal stop disk 1112, and proximal structural backbones 1113. The proximal base disk 1111 and the proximal stop disk 1112 are arranged at an interval. Proximal ends of the plurality of proximal structural backbones 1113 are fixedly connected to the proximal stop disk 1112, and distal ends of the plurality of proximal structural backbones 1113 pass through the proximal base disk 1111. The distal continuum 112 may include a distal base disk 1121, a distal stop disk 1122, and distal structural backbones 1123. The distal base disk 1121 and the distal stop disk 1122 are arranged at an interval, and the distal base disk 1121 is adjacent to the proximal base disk 1111. Distal ends of the plurality of distal structural backbones 1123 are fixedly connected to the distal stop disk 1122, and proximal ends of the plurality of distal structural backbones 1123 pass through the distal base disk 1121 and are then fixedly connected to or integrally formed with the plurality of proximal structural backbones 1113. The drive connection part 120 is connected to the proximal stop disk 1112. The drive connection part 120 comprises an input end located at the proximal side of the proximal stop disk 1112. The input end is for being driven by the drive transmission mechanism such that the proximal stop disk 1112 turns to push and pull the proximal structural backbones 1113, so that the distal continuum 112 bends in a space in different directions. In some embodiments, a distal end of the drive connection part 120 is connected to the proximal base disk 1111, and a proximal end of the drive connection part 120 passes through the proximal stop disk 1112 and is connected to the proximal stop disk 1112, as shown in FIG. 1.

As shown in FIG. 1, in some embodiments, the flexible continuum structure 110 may further include a structural backbone guide tube bundle 113. A proximal end of the structural backbone guide tube bundle 113 is fixedly connected to the proximal base disk 1111, a distal end of the structural backbone guide tube bundle 113 is fixedly connected to the distal base disk 1121, and the distal ends of the plurality of proximal structural backbones 1113 sequentially pass through the proximal base disk 1111 and the structural backbone guide tube bundle 113 and are then respectively connected to the plurality of distal structural backbones 1123. The structural backbone guide tube bundle 113 may guide and constrain a plurality of proximal structural backbones 1113 located between the proximal base disk 1111 and the distal base disk 1121.

Figure 2A:
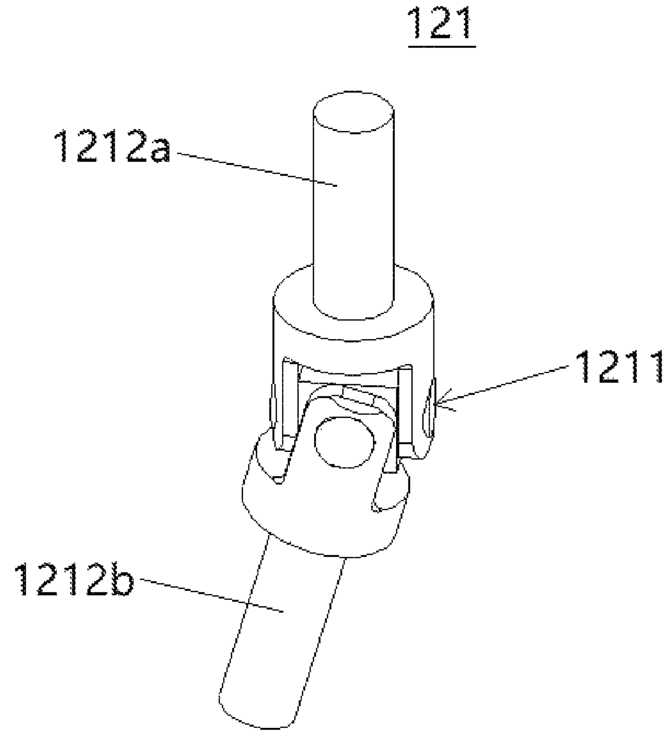
FIG. 2(*a*) shows a schematic structural diagram of a universal coupling joint according to some embodiments of the present disclosure.
Figure 2B:
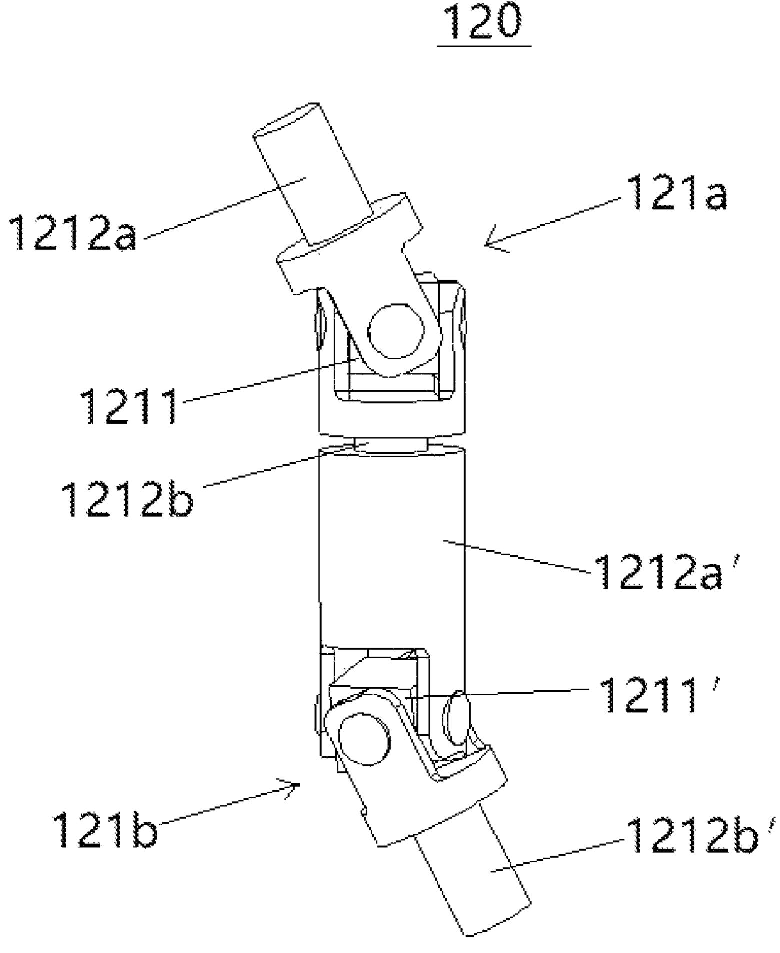

In some embodiments, the drive connection part 120 may include at least one joint, such as a universal coupling joint, a spherical hinge joint, a universal coupling-spherical hinge joint, or a hinge joint. The drive connection part 120 may include multiple universal coupling joints. FIG. 2(*a*) shows a schematic structural diagram of a universal coupling joint 121 according to some embodiments of the present disclosure, and FIG. 2(*b*) shows a schematic structural diagram of a drive connection part 120 according to some embodiments of the present disclosure. In some embodiments, as shown in FIG. 2(*a*), the universal coupling joint 121 may include one universal coupling 1211 or multiple universal couplings 1211 (e.g., multiple universal couplings connected in series), and the one or multiple universal couplings 1211 are located between the proximal base disk 1111 and the proximal stop disk 1112. The universal coupling 1211 may include two rotating pairs which have axes of rotation intersecting each other. In some embodiments, as shown in FIG. 2(*a*), the universal coupling joint 121 may include at least one universal coupling 1211 and at least one link rod. In some embodiments, as shown in FIG. 2(*a*), the universal coupling joint 121 may include a link rod 1212*a* located at a distal end, a link rod 1212*b* located at a proximal end, and a universal coupling 1211 located between the link rods 1212*a-b*. In some embodiments, the universal coupling joint 121 may include the universal coupling 1211 located at the distal end and the link rod 1212*b* located at the proximal end.

In some embodiments, as shown in FIG. 2(*b*), the drive connection part 120 may include at least one distal universal coupling joint 121*a* and at least one proximal universal coupling joint 121*b*. The distal universal coupling joint 121*a* may include a link rod 1212*a*, a link rod 1212*b*, and a universal coupling 1211 located between the link rods 1212*a-b*. The proximal universal coupling joint 121*b* may include a link rod 1212*a*', a link rod 1212*b*', and a universal coupling 1211' located between the link rods 1212*a*' and 1212*b*'. The link rod 1212*a* at the distal end of the distal universal coupling joint 121*a* (at the distal end of the drive connection part 120) is connected to the proximal base disk 1111. The universal coupling 1211 is located between the proximal base disk 1111 and the proximal stop disk 1112. The link rod 1212*b* at the proximal end of the distal universal coupling joint 121*a* is connected to the link rod 1212*a*' at the distal end of the proximal universal coupling joint 121*b*. An outer circular surface of the link rod 1212*a*' or the link rod 1212*b* passes through the proximal stop disk 1112. The universal coupling 1211' is located at the proximal side of the proximal stop disk 1112, and forms the input end of the drive connection part 120 with the link rod 1212*b*' connected to the universal coupling 1211'.

Figure 3:
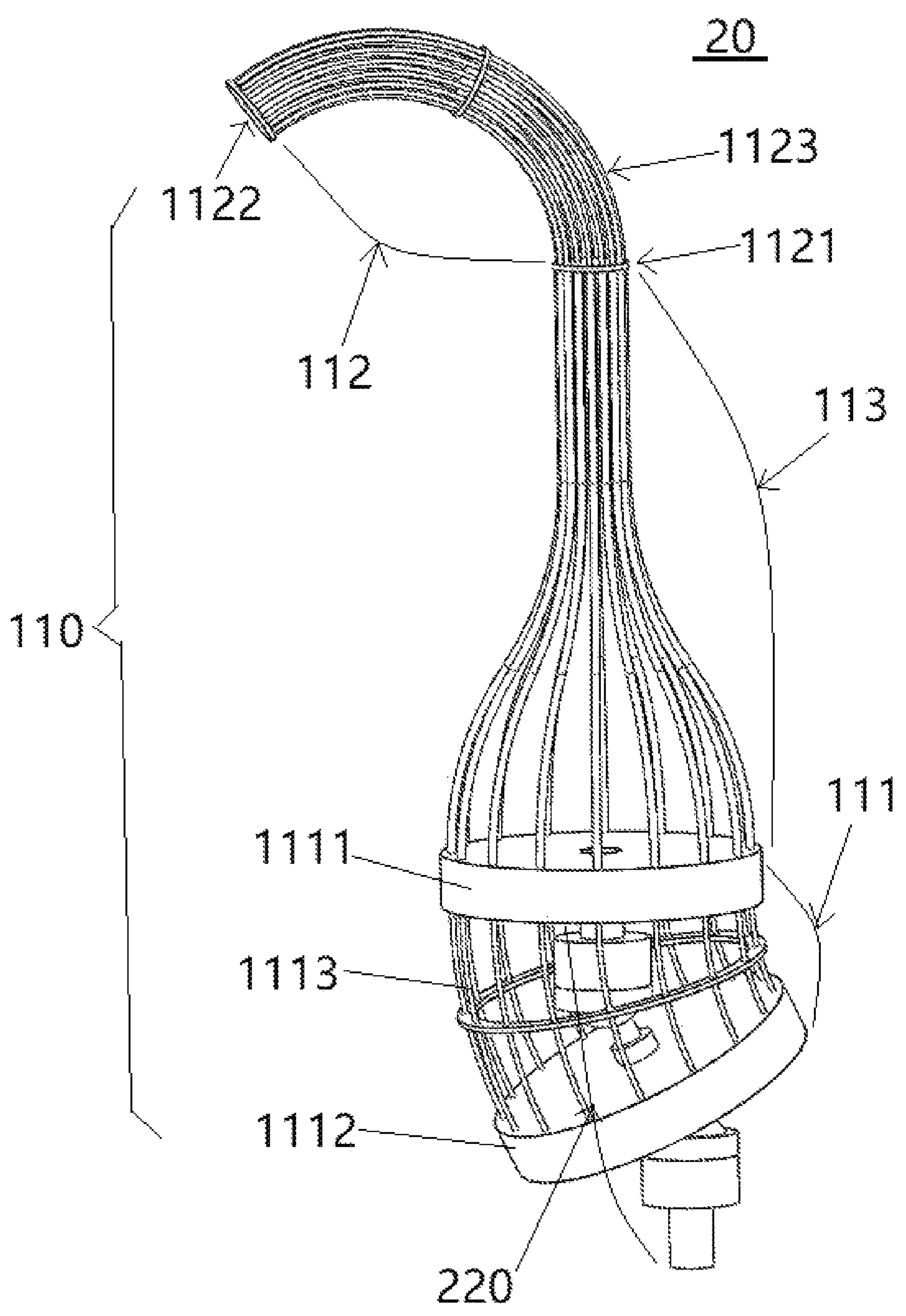
FIG. 3 shows a schematic structural diagram of another continuum instrument according to some embodiments of the present disclosure.
Figure 4A:
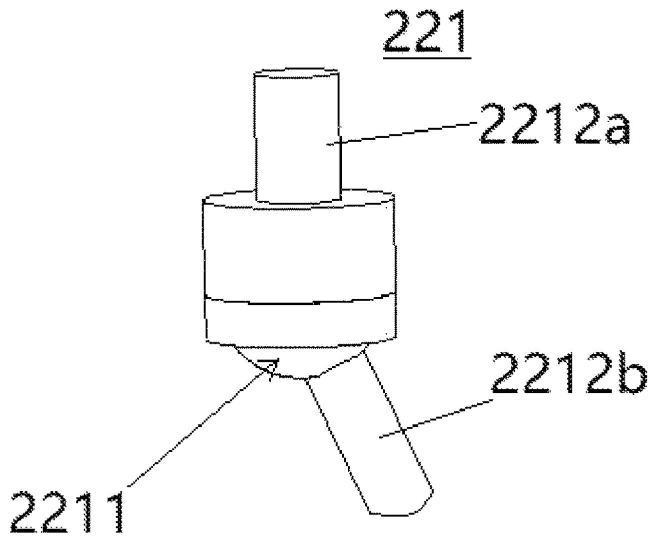
FIG. 4(*a*) shows a schematic structural diagram of a spherical hinge joint according to some embodiments of the present disclosure.
Figure 4B:
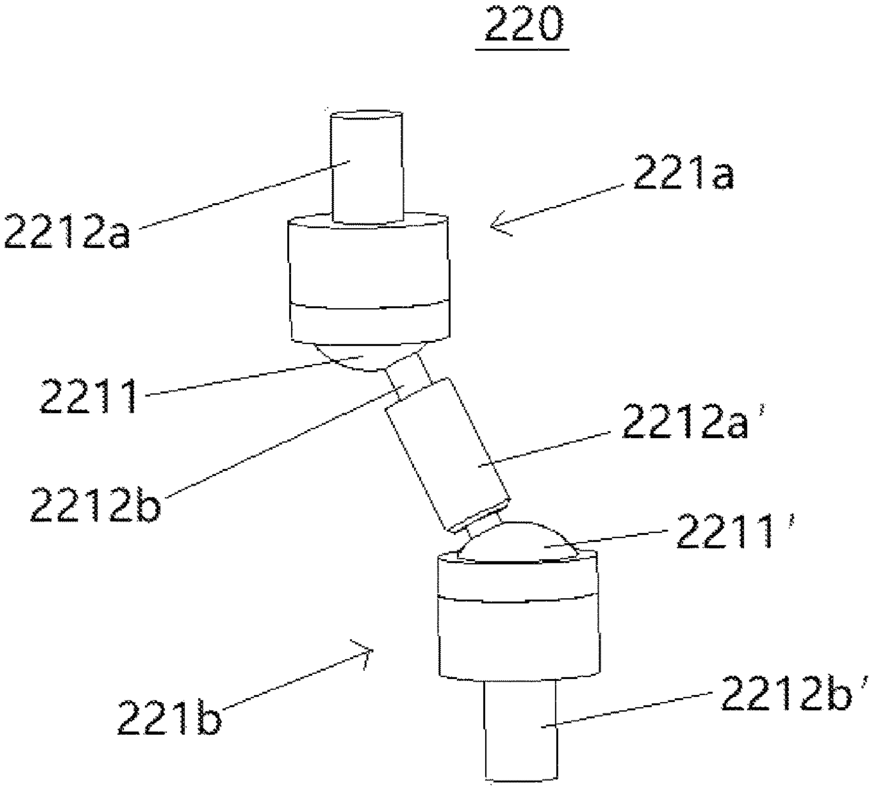

FIG. 3 shows a continuum instrument 20 according to some embodiments of the present disclosure. As shown in FIG. 3, the continuum instrument 20 may include a flexible continuum structure 110 and a drive connection part 220. The drive connection part 220 may include multiple spherical hinge joints. FIG. 4(*a*) shows a schematic structural diagram of a spherical hinge joint 221 according to some embodiments of the present disclosure, and FIG. 4(*b*) shows a schematic structural diagram of a drive connection part 220 according to some embodiments of the present disclosure. In some embodiments, as shown in FIG. 4(*a*), the spherical hinge joint 221 may include one spherical hinge 2211 or multiple spherical hinges 2211 (e.g., multiple spherical hinges 2211 connected in series). At least one spherical hinge 2211 is located between the proximal base disk 1111 and the proximal stop disk 1112. The spherical hinge 2211 may include three rotating pairs which have axes of rotation intersecting each other. In some embodiments, the spherical hinge joint 221 in FIG. 4(*a*) may include at least one spherical hinge 2211 and at least one link rod. In some embodiments, as shown in FIG. 4(*a*), the spherical hinge joint 221 may include a link rod 2212*a* located at a distal end, a link rod 2212*b* located at a proximal end, and the spherical hinge 2211 located between the link rods 2212*a-b*. In some embodiments, the spherical hinge joint 221 may include a spherical hinge 2211 located at the distal end and a link rod 2212*b* located at the proximal end.

In some embodiments, as shown in FIG. 4(*b*), the drive connection part 220 may include at least one distal spherical hinge joint 221*a* and at least one proximal spherical hinge joint 221*b*. The distal spherical hinge joint 221*a* may include link rods 2212*a-b* and a spherical hinge 2211 located between the link rods 2212*a-b*. The proximal spherical hinge joint 221*b* may include a link rod 2212*a*', a link rod 2212*b*', and a spherical hinge 2211' located between the link rods 2212*a*' and 2212*b*'. The link rod 2212*a* at the distal end of the distal spherical hinge joint 221*a* is connected to the proximal base disk 1111. The spherical hinge 2211 is located between the proximal base disk 1111 and the proximal stop disk 1112. The link rod 2212*b* at the proximal end of the distal spherical hinge joint 221*a* is connected to the link rod 2212*a*' at the distal end of the proximal spherical hinge joint 221*b*. An outer circular surface of the link rod 2212*a*' or the link rod 2212*b* passes through the proximal stop disk 1112 and is connected to the proximal stop disk 1112. The spherical hinge 2211' is located at the proximal side of the proximal stop disk 1112, and forms the input end of the drive connection part 220 with the link rod 2212*b*' connected to the spherical hinge 2211'.

Figure 5:
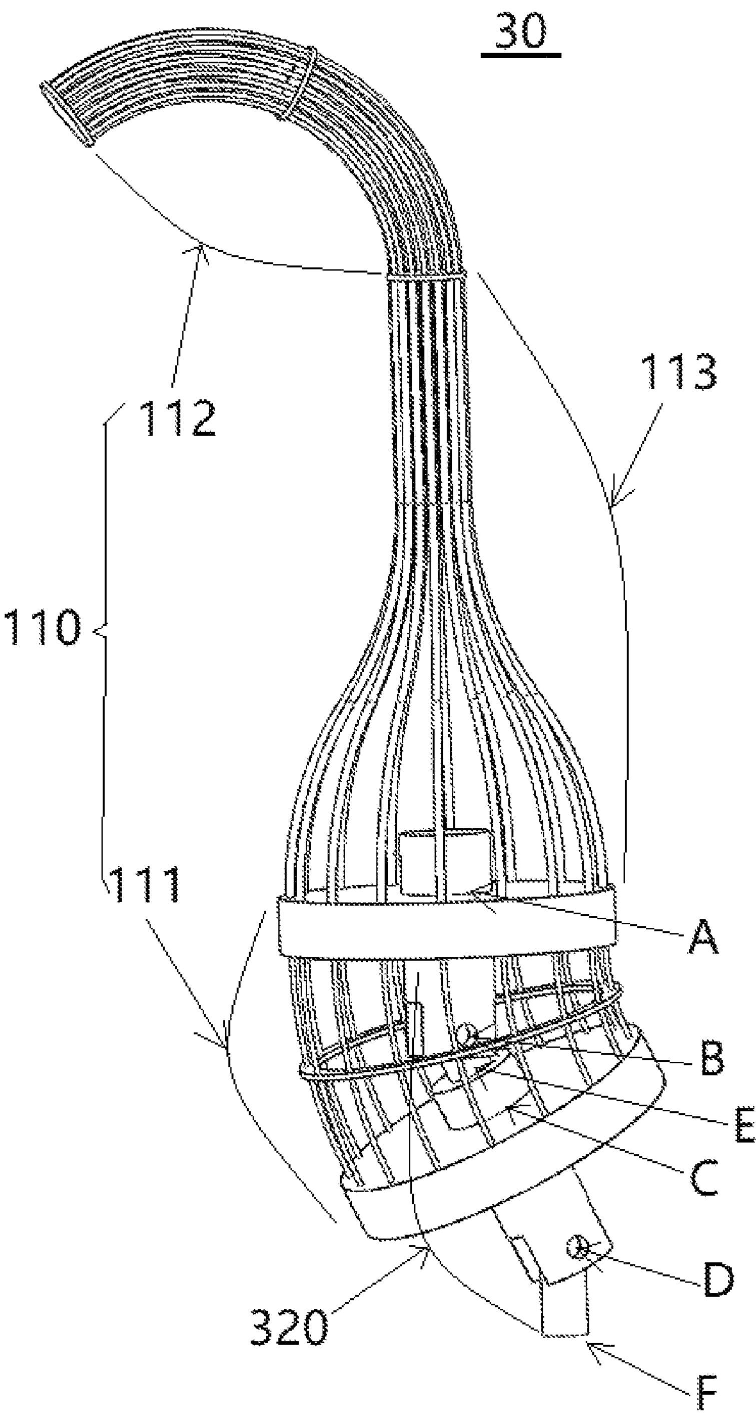
FIG. 5 shows a schematic structural diagram of another continuum instrument according to some embodiments of the present disclosure.
Figure 6:
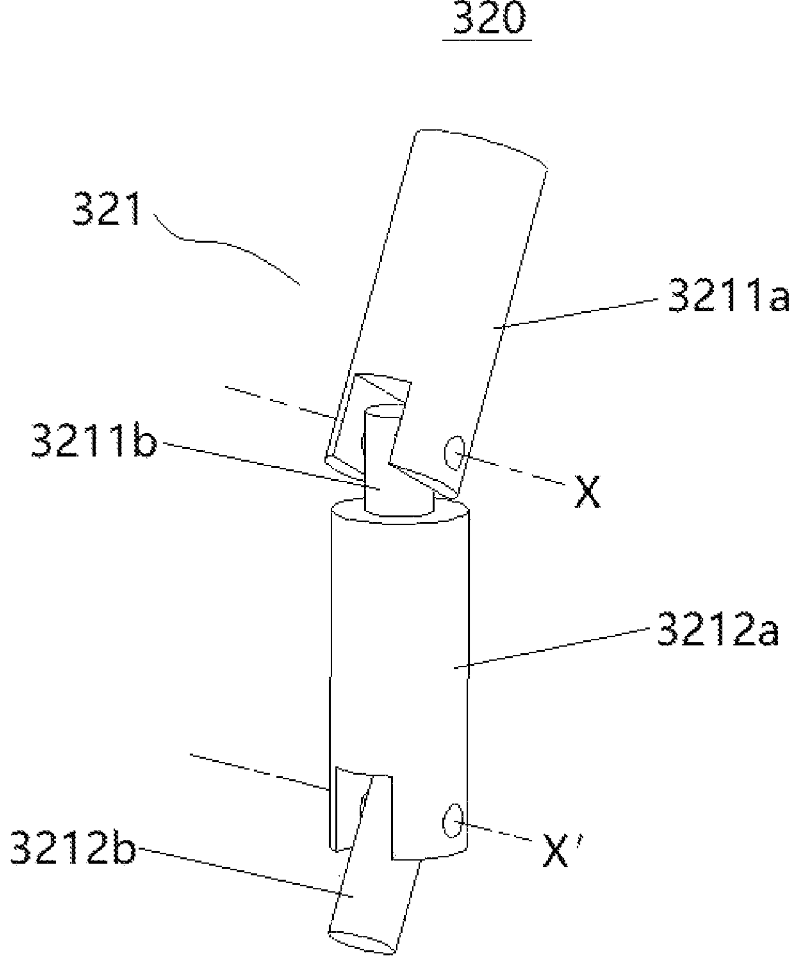
FIG. 6 shows a schematic structural diagram of another drive connection part according to some embodiments of the present disclosure.

FIG. 5 shows a continuum instrument 30 according to some embodiments of the present disclosure. As shown in FIG. 5, the continuum instrument 30 may include a flexible continuum structure 110 and a drive connection part 320. FIG. 6 shows a schematic structural diagram of the drive connection part 320 according to some embodiments of the present disclosure. As shown in FIG. 6, the drive connection part 320 may include a hinge joint 321. In some embodiments, the hinge joint 321 may include at least one distal link rod and at least one proximal link rod hinged to each other. As shown in FIG. 6, in some embodiments, the hinge joint 321 may include, for example, a multi-link hinge joint including, for example, a distal link rod 3211*a*, a distal link rod 3211*b*, a proximal link rod 3212*a*, and a proximal link rod 3212*b*. A distal end of the distal link rod 3211*a* is connected to the proximal base disk 1111, a proximal end of the distal link rod 3211*a* is hinged to a distal end of the distal link rod 3211*b*, a proximal end of the distal link rod 3211*b* is connected to a distal end of the proximal link rod 3212*a*, an outer circular surface of the distal link rod 3211*b* or the proximal link rod 3212*a* passes through the proximal stop disk 1112 and is connected to the proximal stop disk 1112, a proximal end of the proximal link rod 3212*a* is hinged to a distal end of the proximal link rod 3212*b*, and the proximal link rod 3212*b* forms the input end of the drive connection part 320. The hinge axes X of the distal link rods 3211*a* and

3211*b* are perpendicular to the axial directions of the distal link rods 3211*a-b*, the hinge axes X' of the proximal link rods 3212*a* and 3212*b* are perpendicular to the axial directions of the proximal link rods 3212*a-b*, and the hinge axis X and the hinge axis X' are parallel to each other.

In some embodiments, one of the universal couplings 1211 and 1211' in the drive connection part 120 may be replaced with a spherical hinge 2211 or 2211', or one of the spherical hinges 2211 and 2211' in the drive connection part 220 may be replaced with the universal coupling 1211 or 1211' to form a universal coupling-spherical hinge joint (not shown). In some embodiments, the universal coupling-spherical hinge joint may include at least one universal coupling joint 121*a* located at the distal end and at least one spherical hinge joint 221*b* located at the proximal end. In some embodiments, the universal coupling-spherical hinge joint may include at least one spherical hinge joint 221*a* located at the distal end and at least one universal coupling joint 121*b* located at the proximal end.

Figure 7:
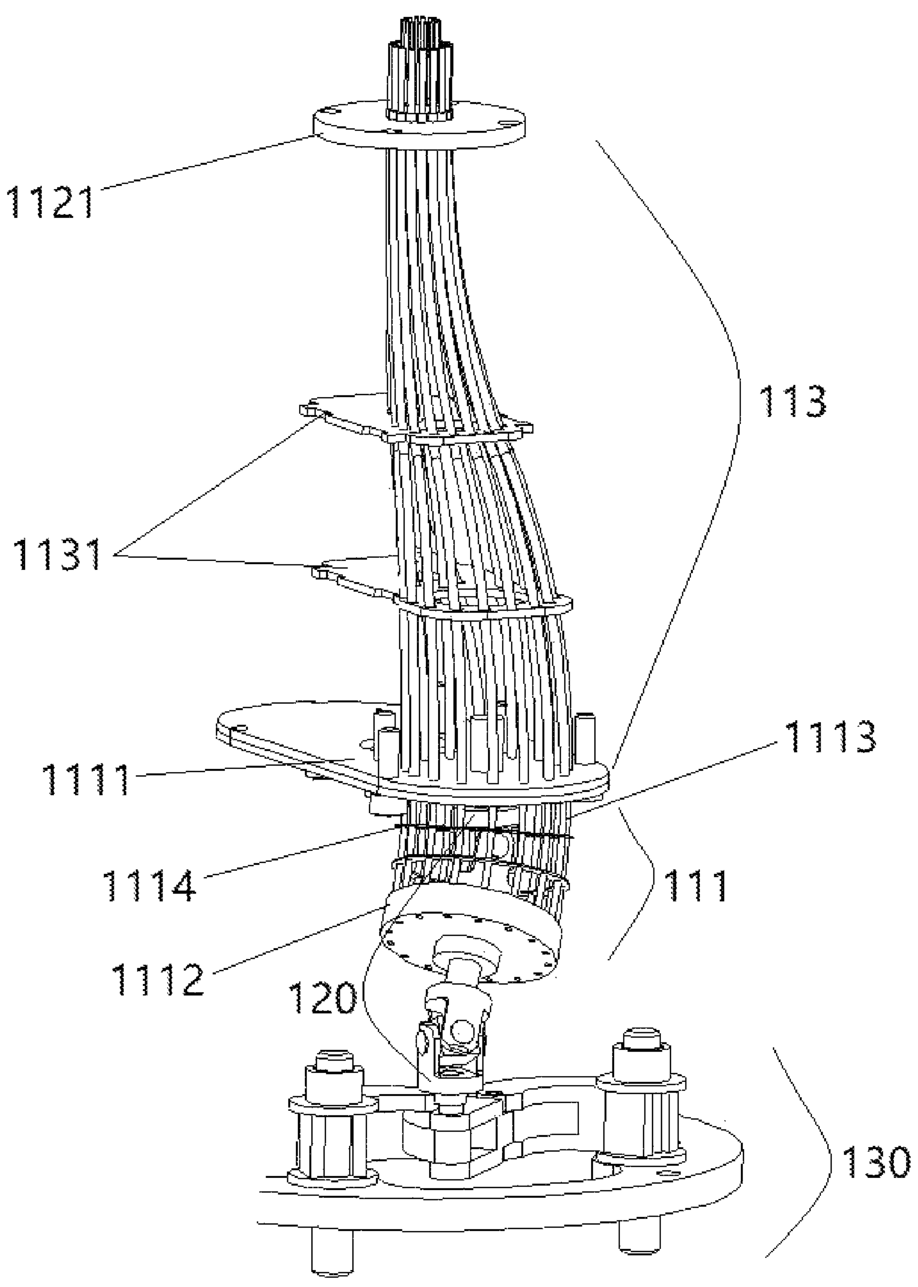
FIG. 7 shows a partial schematic structural diagram of another continuum instrument according to some embodiments of the present disclosure.
Figure 8:
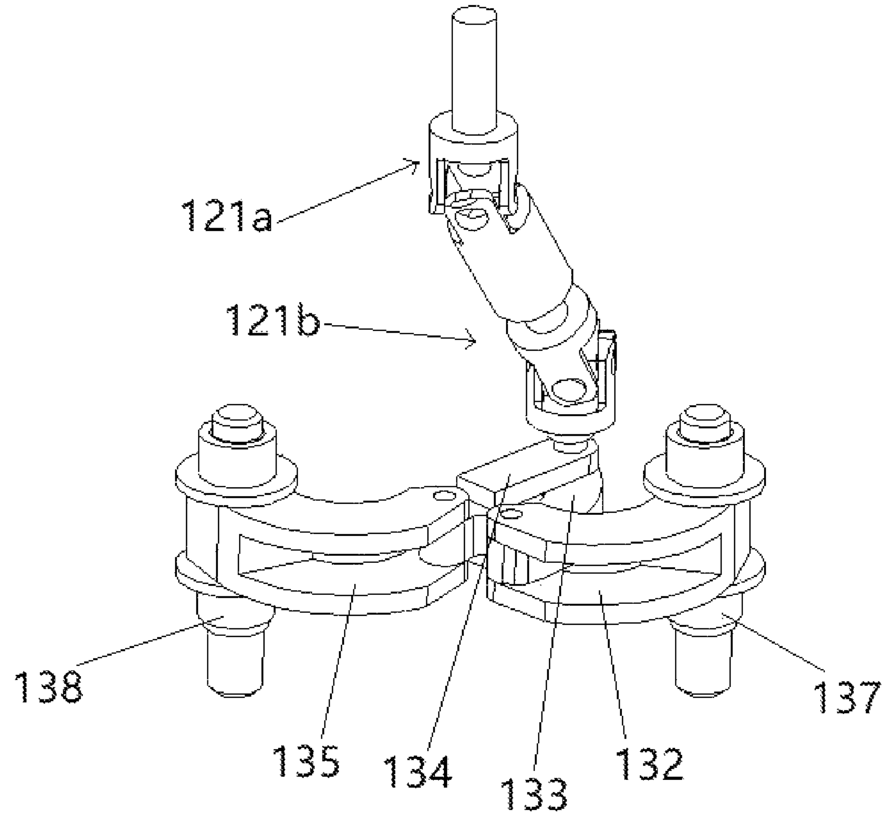
FIG. 8 shows a partial schematic structural diagram of the continuum instrument shown in FIG. 7 according to some embodiments of the present disclosure.
Figure 9:
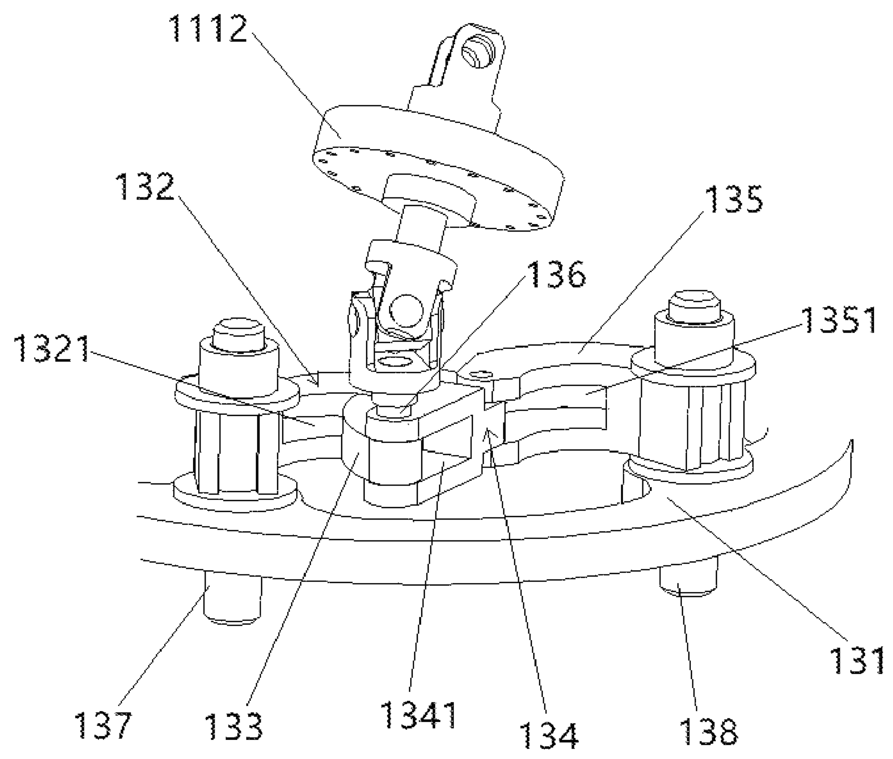
FIG. 9 shows a schematic structural diagram of the drive transmission mechanism shown in FIG. 7 according to some embodiments of the present disclosure.
Figure 10:
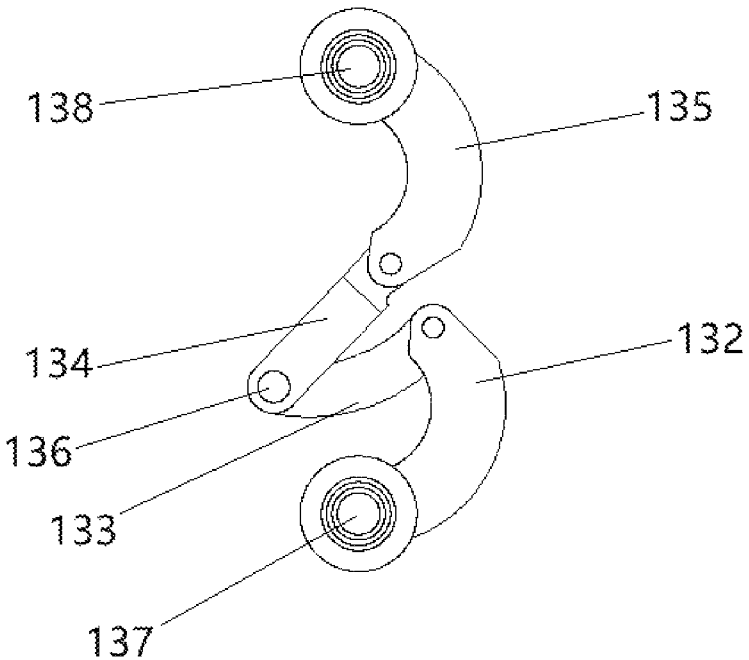
FIG. 10 shows a partial structural top view of the drive transmission mechanism shown in FIG. 9 according to some embodiments of the present disclosure.

In some embodiments, the continuum instrument 10 (or 20, 30) may further include a drive transmission mechanism. An output end of the drive transmission mechanism may move in a planar motion. FIGS. 7 and 8 respectively show a partial schematic structural diagram of a continuum instrument 10 (or 20, 30) according to some embodiments of the present disclosure including a drive transmission mechanism 130. FIGS. 9 and 10 respectively shows a schematic structural diagram and a partial structural top view of the drive transmission mechanism 130 according to some embodiments of the present disclosure. In some embodiments, as shown in FIGS. 7-9, the drive transmission mechanism 130 may include a planar link mechanism, which may include a first connecting rod 131, a second connecting rod 132, a third connecting rod 133, a fourth connecting rod 134, a fifth connecting rod 135, an output shaft 136, a first input shaft 137, and a second input shaft 138. The first connecting rod 131 is fixedly disposed, and the first input shaft 137 and the second input shaft 138 are rotatably disposed on the first connecting rod 131. One end of the second connecting rod 132 is fixedly connected to the first input shaft 137, and the other end of the second connecting rod 132 is hinged to one end of the third connecting rod 133. One end of the fifth connecting rod 135 is fixedly connected to the second input shaft 138, and the other end of the fifth connecting rod 135 is hinged to one end of the fourth connecting rod 134. The other end of the fourth connecting rod 134 is hinged to the other end of the third connecting rod 133, and is hinged to the output shaft 136. The output shaft 136 is connected to the input end of the drive connection part 120 (or 220, 320).

In some embodiments, as shown in FIGS. 9 and 10, the first connecting rod 131 may include an arc-shaped link rod formed by a base, the second connecting rod 132 and the fifth connecting rod 135 may be arc-shaped, and the second connecting rod 132 and the fifth connecting rod 135 have one end respectively fixedly connected to the first input shaft 137 and the second input shaft 138, and thus can rotate along with the rotation of the first input shaft 137 and the second input shaft 138. In some embodiments, the third connecting rod 133 may be arc-shaped, and the fourth connecting rod 134 may be straight. By means of the cooperation of the arc-shaped link rod and the straight link rod, the output shaft 136 may move in a horizontal plane in any direction. As shown in FIG. 9, the second connecting rod 132 may include an arc-shaped opening 1321, and the fifth connecting rod 135 may include an arc-shaped opening 1351. One end of the third connecting rod 133 is located in the arc-shaped opening and is hinged to the other end of the second connecting rod 132. One end of the fourth connecting rod 134 is located in the arc-shaped opening and hinged to the other end of the fifth connecting rod 135. The fourth connecting rod 134 may include an opening, and the other end of the third connecting rod 133 is located in the opening and hinged to the other end of the fourth connecting rod 134. The configuration of the arc-shaped openings and the opening may facilitate the rotation of the third connecting rod 133 and the fourth connecting rod 134. It should be appreciated that the connecting rods may also be hinged to each other on the surfaces of or outside the connecting rods, which can also achieve the free rotation of the connecting rods.

Thus, as shown in FIGS. 7-9, when the first input shaft 137 and/or the second input shaft 138 is/are driven to rotate, the second connecting rod 132 and the fifth connecting rod 135 are driven to rotate, the third connecting rod 133 and the fourth connecting rod 134 are then driven to rotate, and thus the output shaft 136 of the planar five-rod mechanism is driven to freely move in the plane, so that the input end of the drive connection part 120 (or 220, 320) is driven to move by means of the output shaft 136 so as to drive the proximal stop disk 1112 to slide up and down and turn relative to the drive connection part 120, so that the proximal base disk 1111 and the proximal stop disk 1112 are out of alignment, with the axes of the two no longer coincident. The proximal stop disk 1112 turns so as to push and pull a plurality of proximal structural backbones 1113 which have ends fixed to the proximal stop disk 1112, so that the plurality of proximal structural backbones 1113 fixed to (e.g., uniformly distributed on) the proximal stop disk 1112 are pulled on one side to increase the corresponding lengths of the proximal structural backbones 1113 in the proximal continuum 111 and are pushed on the other side to decrease the corresponding lengths of the proximal structural backbones 1113 in the proximal continuum 111. Since the overall length of the proximal structural backbones 1113 is substantially unchanged, resulting in a corresponding change in the length of the distal structural backbones 1123 in the distal continuum 112, the distal continuum 112 is thus driven to bend corresponding to (e.g., in the same direction, in an opposite direction, or angled with) the proximal continuum 111. The proximal stop disk 1112 is driven to turn so as to push and pull the proximal structural backbones 1113 and the distal structural backbones 1123, which replaces the direct pushing and pulling for the proximal structural backbones 1113 and the distal structural backbones 1123. A large number of structural backbones can be driven without being limited by the number of the drive transmission mechanisms, achieving a compact structure and very high reliability and flexibility.

It should be noted that the proportions of bending of the proximal continuum 111 and the distal continuum 112 are respectively inversely proportional to the corresponding distribution radii of the proximal structural backbones 1113 and the distal structural backbones 1123 in the two continua (in this embodiment, the proximal structural backbones 1113 in the proximal continuum 111 and the distal structural backbones 1123 in the distal continuum 112 are respectively distributed in a circumferential direction, may be distributed on a circumference or in a peripheral direction of a rectangular, polygonal, elliptical or other shape, and may be in a uniform or non-uniform distribution). Therefore, when in use, the distribution radii of the proximal structural backbones 1113 and the distal structural backbones 1123 in the proximal continuum 111 and the distal continuum 112 may be respectively adjusted to meet the actual requirements of the proportion of bending.

Figure 11:
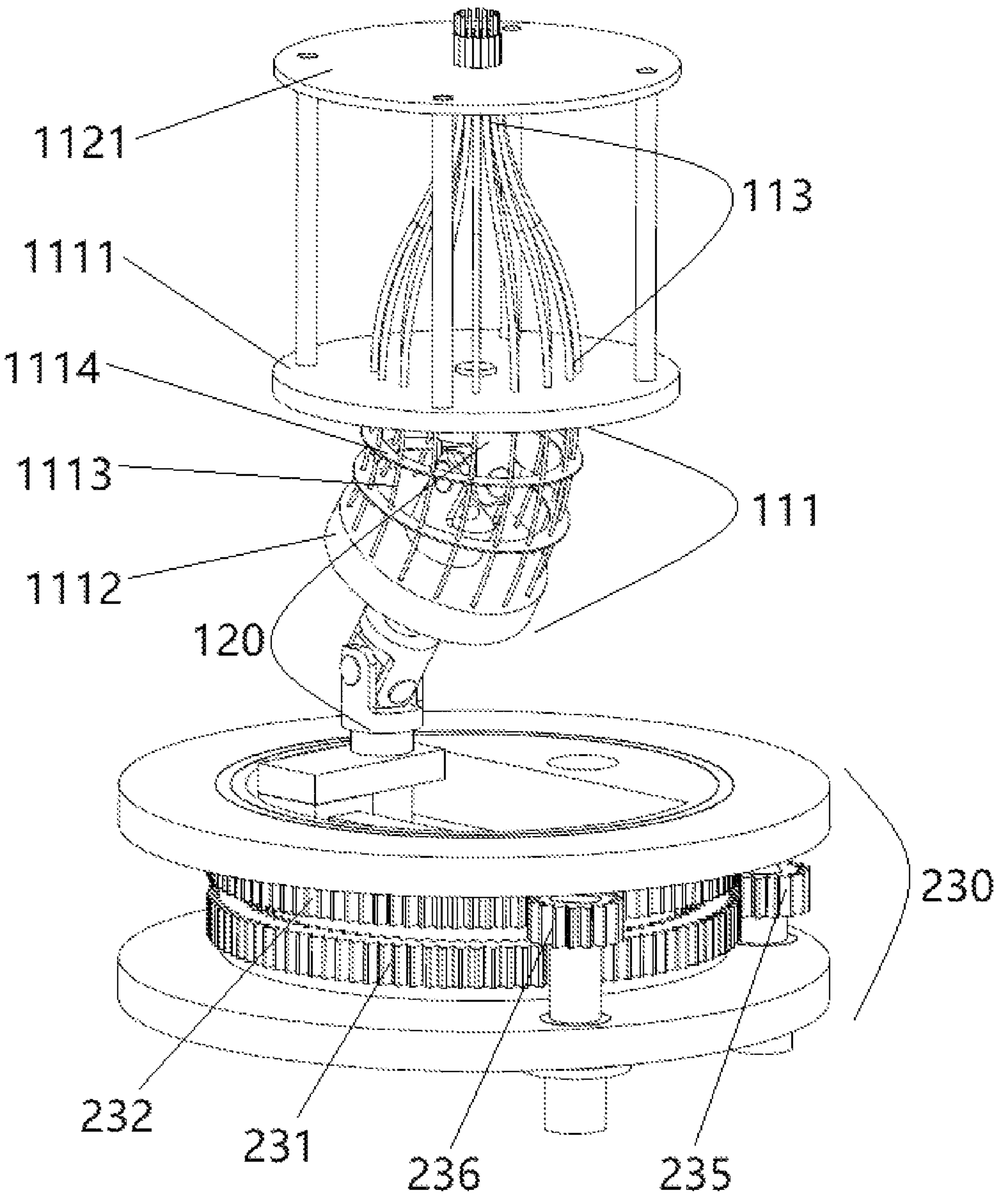
FIG. 11 shows a partial schematic structural diagram of another continuum instrument according to some embodiments of the present disclosure.
Figure 12:
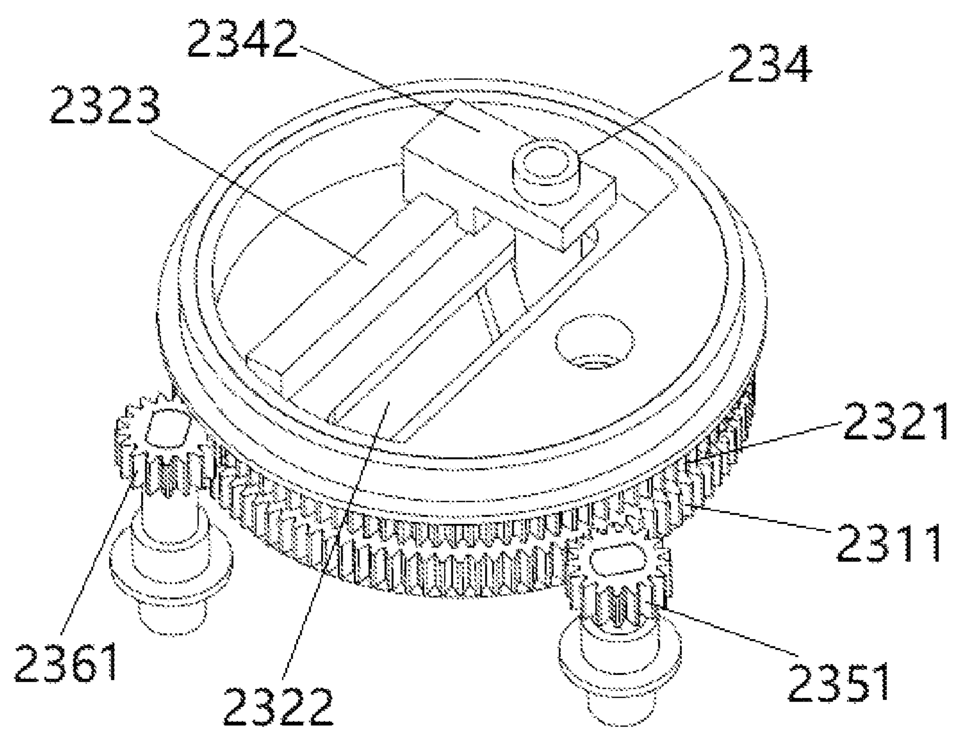
FIG. 12 shows a schematic structural diagram of a drive transmission mechanism shown in FIG. 11 according to some embodiments of the present disclosure.
Figure 13:
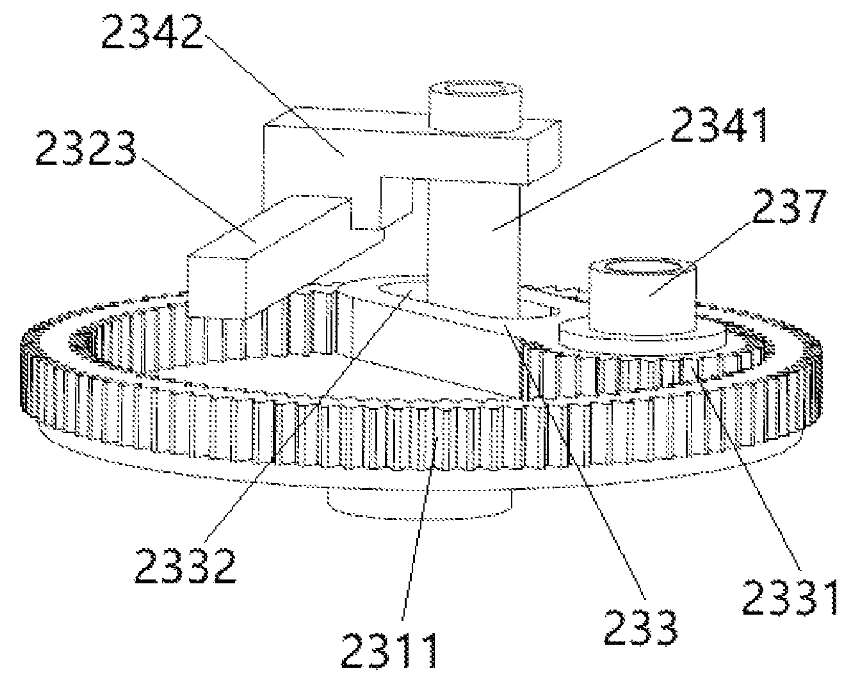
FIG. 13 shows a partial schematic structural diagram of the drive transmission mechanism shown in FIG. 12 according to some embodiments of the present disclosure.

FIG. 11 shows a partial schematic structural diagram of the continuum instrument 10 (or 20, 30) according to some embodiments of the present disclosure including a drive transmission mechanism 230. FIG. 12 shows a schematic structural diagram of the drive transmission mechanism 230 according to some embodiments of the present disclosure, and FIGS. 13 and 14 respectively show a partial schematic structural diagram of the drive transmission mechanism 230 according to some embodiments of the present disclosure. In some embodiments, as shown in FIGS. 11-14, the drive transmission mechanism 230 may include a gear and sliding groove mechanism, and the gear and sliding groove mechanism may include a first rotatable member 231, a moving member 233, a second rotatable member 232, and a sliding assembly 234. The first rotatable member 231 may be used for being driven by the first drive member 235 to rotate around its own center of rotation, the moving member 233 may be used for being driven by the rotation of the first rotatable member 231 to rotate around its own center of rotation, and the center of rotation of the moving member 233 is offset from the center of rotation of the first rotatable member 231, and the moving member 233 is provided with a first sliding guide portion 2332, as shown in FIG. 13. The second rotatable member 232 is coaxially disposed with the first rotatable member 231 and may be used for being driven by the second drive member 236 to rotate relative to the first rotatable member 231, and the second rotatable member 232 is provided with a second sliding guide portion 2322. As shown in FIGS. 12 and 13, the sliding assembly 234 is slidably connected to the first sliding guide portion 2332 and the second sliding guide portion 2322 to slide along the first sliding guide portion 2332 and the second sliding guide portion 2322, and the sliding assembly 234 is connected to the input end of the drive connection part 120 (or 220, 320).

In some embodiments, as shown in FIG. 12, the second rotatable member 232 may be arranged above the first rotatable member 231 in an overlapping manner, and the two rotatable members are rotatable relative to each other. As shown in FIGS. 11 and 12, in some embodiments, the first rotatable member 231 may include, for example, a first driven gear 2311. The first drive member 235 may include a first driving gear 2351. The second rotatable member 232 may include, for example, a second driven gear 2321. The second drive member 236 may include a second driving gear 2361. The first driving gear 2351 meshes with the first driven gear 2311, the second driving gear 2361 meshes with the first driven gear 2311, and the second driven gear 2321 is arranged above the first driven gear 2311 in an overlapping manner. The first driving gear 2351 may be driven by a drive electric motor to drive the first driven gear 2311 to rotate. The second driving gear 2361 may be driven by the drive electric motor to drive the second driven gear 2321 to rotate, and the first driven gear 2311 and the second driven gear 2321 are rotatable relative to each other. In some embodiments, the first rotatable member 231 and the second rotatable member 232 may respectively include a first gear and a second gear, the first drive member 235 and the second drive member 236 may include a drive electric motor (or a motor), and the first gear and the second gear can be respectively driven by the drive electric motor to rotate relative to each other. In some embodiments, the transmission mode of the first rotatable member 231 and the second rotatable member 232 may also be other transmission modes, such as belt pulley transmission or sprocket transmission.

In some embodiments, as shown in FIG. 13, the moving member 233 may include a meshing portion 2331. The meshing portion 2331 is for meshing with the first rotatable member 231. In some embodiments, the moving member 233 may be a link rod having at least one end portion which is circular arc-shaped. The meshing portion 2331 may include teeth disposed on an outer peripheral surface of the circular arc-shaped end portion. An inner peripheral surface of the first rotatable member 231 (e.g., the first driven gear 2311) is provided with inner ring teeth 2312, and the teeth of the outer peripheral surface of the circular arc-shaped end portion mesh with the inner ring teeth 2312 of the first rotatable member 231 so that, when the first rotatable member 231 rotates, the moving member 233 is driven to rotate with the first rotatable member 231. It should be noted that in some embodiments, a further gear (not shown) may be provided in the first rotatable member 231, and the further gear coaxially and synchronously rotates with the first rotatable member 231, and the teeth on the outer peripheral surface of the moving member 233 mesh with the further gear, so that the moving member 233 can be driven by the first rotatable member 231 to rotate.

In some embodiments, as shown in FIGS. 12 and 13, the moving member 233 is provided with a first sliding guide portion 2332. The first sliding guide portion 2332 may include a first sliding groove disposed in the lengthwise direction of the moving member 233. The second rotatable member 232 (e.g., the second driven gear 2321) is provided with a second sliding guide portion 2322, and the second sliding guide portion 2322 may include a second sliding groove formed along the diameter of the second rotatable member 232. The sliding assembly 234 may include a sliding pin 2341. The sliding pin 2341 is slidably disposed in the first sliding groove and the second sliding groove, a distal end of the sliding pin 2341 is connected to the input end of the drive connection part 120 (or 220, 320), so that the sliding pin 2341 can move along the first sliding groove and/or the second sliding groove. In some embodiments, as shown in FIG. 13, the sliding assembly 234 may further include a sliding block 2342 fixedly connected to or integrally formed with the sliding pin 2341. The second rotatable member 232 may be provided with a sliding rail 2323 parallel to the second sliding groove, and the sliding block 2342 is slidably disposed on the sliding rail 2323. For example, the sliding block 2342 and the sliding rail 2323 may be in a groove-type cooperation. A proximal end of the sliding pin 2341 is slidably disposed in the first sliding groove, and a distal end thereof passes through the first sliding groove and the second sliding groove and is then fixedly connected to the sliding block 2342. The distal end of the sliding pin 2341 may pass through the sliding block 2342 and is then connected to the input end of the drive connection part 120, or is connected to the input end of the drive connection part 120 by means of the sliding block 2342. The cooperation of the sliding block 2342 and the sliding rail 2323 can guide the motion of the sliding pin 2341, so that the sliding pin 2341 can move more smoothly.

In some embodiments, the first sliding guide portion 2332 may include a first sliding rail (not shown) disposed in the lengthwise direction of the moving member 233, and the second sliding guide portion 2322 includes a second sliding rail disposed along the diameter of the second rotatable member 232. The sliding assembly 234 may include a first sliding block, a second sliding block, and a sliding pin. The first sliding block is slidably disposed on the first sliding rail, the second sliding block is slidably disposed on the second sliding rail, one of the first sliding block and the second sliding block is disposed to be movably connected to the sliding pin, and the other of the first sliding block and the second sliding block is disposed to be fixedly connected to or integrally formed with the sliding pin. The sliding pin can also slide along the first sliding rail and/or the second sliding rail. It should also be appreciated that one of the first sliding guide portion 2332 and the second sliding guide portion 2322 may include a sliding rail, the other of the first sliding guide portion 2332 and the second sliding guide portion 2322 may include a sliding groove, and the sliding assembly 234 may include a sliding block and a sliding pin fixedly connected to or integrally formed with the sliding block, the sliding pin being disposed in the sliding groove, and the sliding block being slidably disposed on the sliding rail.

Figure 14:
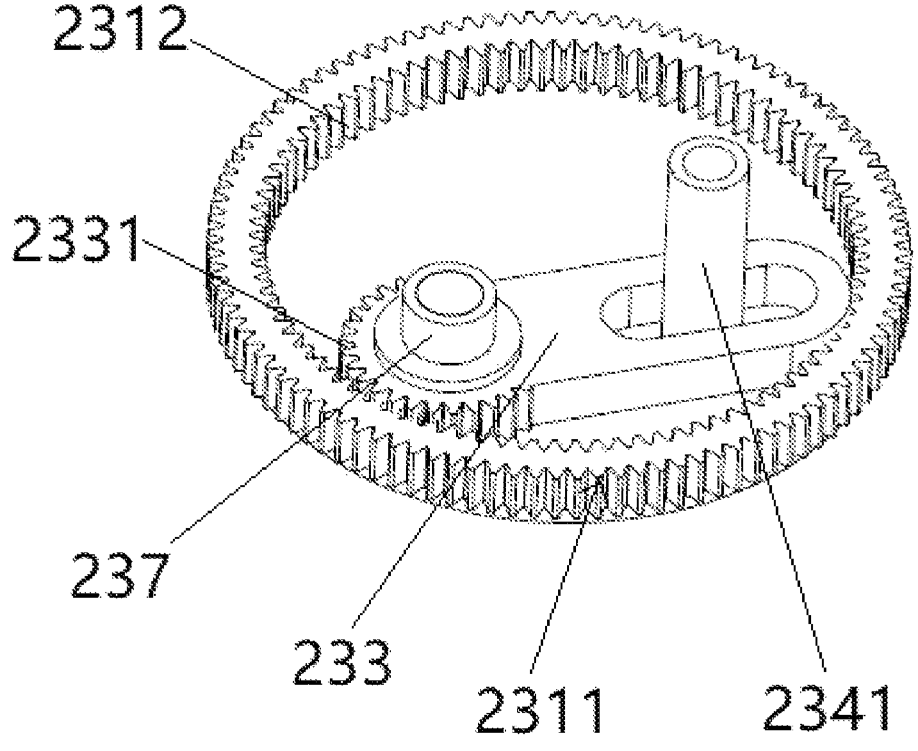
FIG. 14 shows a partial schematic structural diagram of the drive transmission mechanism shown in FIG. 12 according to some embodiments of the present disclosure.

In some embodiments, as shown in FIGS. 13 and 14, the drive transmission mechanism 230 may further include a rotating shaft 237. A proximal end of the rotating shaft 237 may be fixedly connected to or integrally formed with the moving member 233, the rotating shaft 237 may be located at the end close to the circular arc-shaped end portion, and a distal end of the rotating shaft 237 may be rotatably disposed on the second rotatable member 232, so that the rotating shaft 237 may rotate relative to the second rotatable member 232; and the axis of rotation of the rotating shaft 237 is offset from the center of rotation of the second rotatable member 232, so that when the first driven gear 2311 rotates at any angle, the second sliding groove can always intersect the first sliding groove, with the sliding pin 2341 being located at the point of intersection of the two sliding grooves.

Thus, as shown in FIGS. 11, 12 and 13, when the first driving gear 2351 drives the first driven gear 2311 located at the lower layer to rotate while the second driving gear 2361 located at the upper layer remains stationary, the moving member 233 meshing with the first driven gear 2311 is driven to rotate around the rotating shaft 237 so as to drive the sliding pin 2341 located in the first sliding groove and the second sliding groove to move, and the sliding pin 2341 can move linearly along the second sliding groove by means of the limiting cooperation of the second sliding groove and the first sliding groove so as to drive, by means of the sliding pin 2341, the input end of the drive connection part 120 (or 220, 320) to move. Since the proximal stop disk 1112 can be driven by the drive connection part 120 to turn, the proximal base disk 1111 and the proximal stop disk 1112 are out of alignment and have the axes no longer coincident. The proximal stop disk 1112 turns to push and pull the plurality of proximal structural backbones 1113 which have ends fixed to the proximal stop disk 1112, so that the proximal continuum 111 bends and then drive the distal continuum 112 to bend corresponding to (e.g., in the same direction, in an opposite direction, or angled with) the proximal continuum 111, so that the distal continuum 112 can bend in a space along a specific bending plane. The distance that the sliding pin 2341 or the sliding block 2342 moves along the second sliding groove can be adjusted so as to adjust the degree of bending of the proximal continuum 111 to adjust the degree of bending of the distal continuum 112. In the case where the second driving gear 2361 drives the second driven gear 2321 to rotate so that the first driving gear 2351 drives the first driven gear 2311 to rotate, and the second driven gear 2321 and the first driven gear 2311 synchronously rotate in the same direction (e.g., at a same speed), the position of the sliding pin 2341 in the first sliding groove and the second sliding groove does not change, but the azimuth angle of the plane of rotation of the sliding pin 2341 changes (the sliding pin 2341 moves in a circular motion), so as to change the orientation of the bending plane of the input end of the drive connection part 120 (or 220, 320). After the proximal continuum 111 is bent, the push and pull action generated on the proximal structural backbones 1113 is transferred to the distal structural backbones 1123 and the distal continuum 112 by means of the structural backbone guide tube bundle 113, so as to achieve the bending of the distal continuum 112 in a space along different bending planes. The second driven gear 2321 and the first driven gear 2311 are driven cooperatively to adjust the degree of bending of the proximal continuum 111 along the specific bending plane and the bending thereof in different bending planes, so as to achieve the bending of the distal continuum 112 in the space in any direction.

Figure 15:
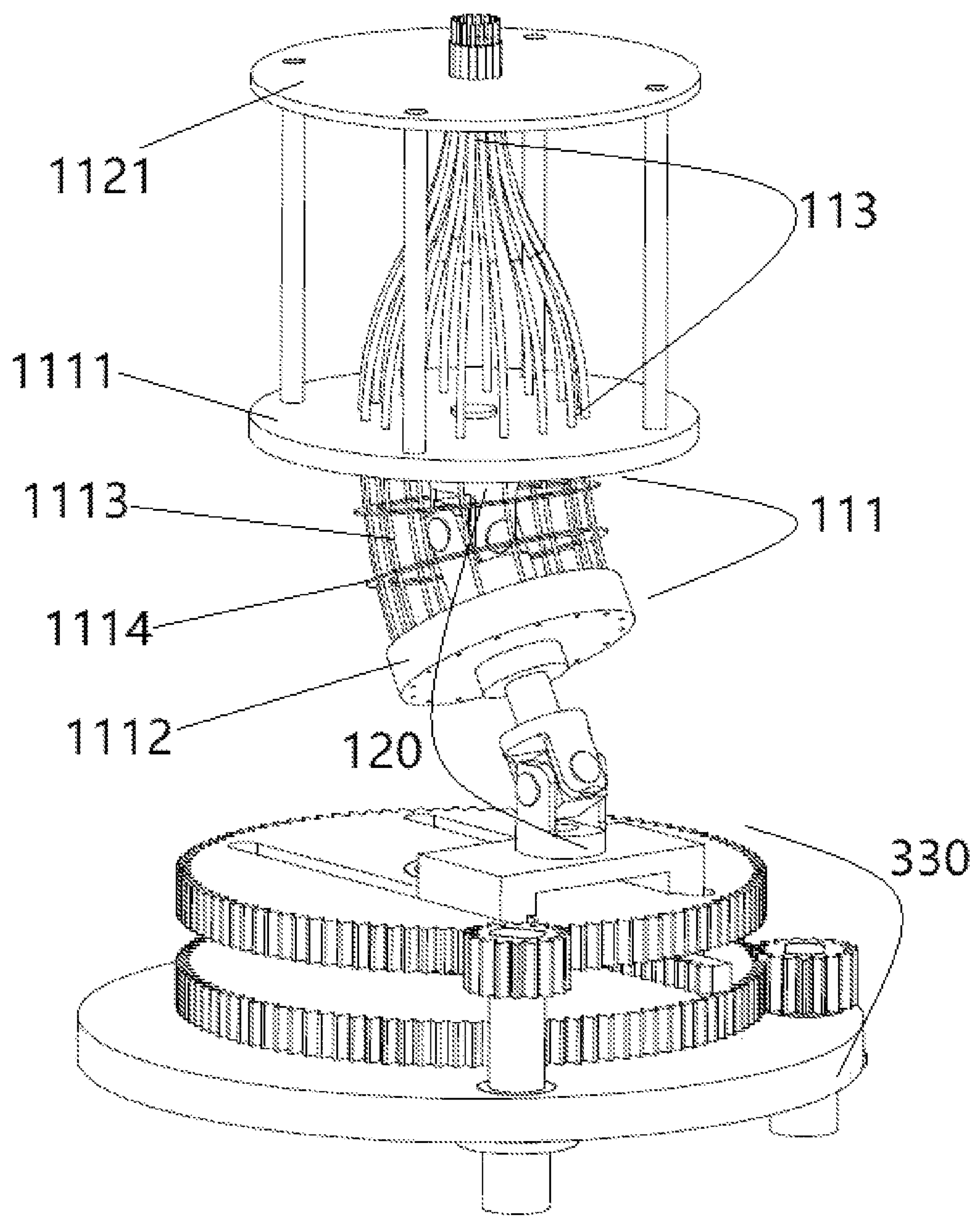
FIG. 15 shows a partial schematic structural diagram of another continuum instrument according to some embodiments of the present disclosure.
Figure 16:
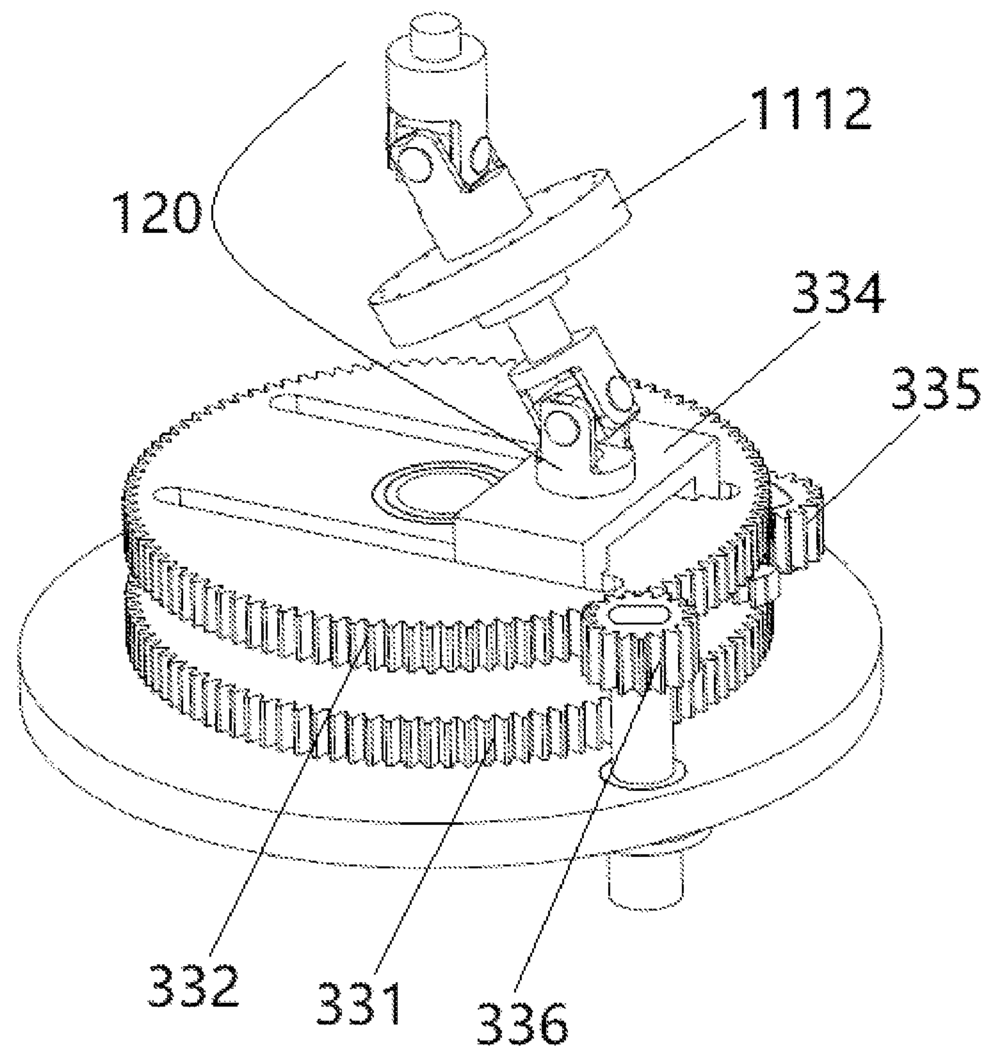
FIG. 16 shows a partial schematic structural diagram of the continuum instrument shown in FIG. 15 according to some embodiments of the present disclosure.
Figure 17:
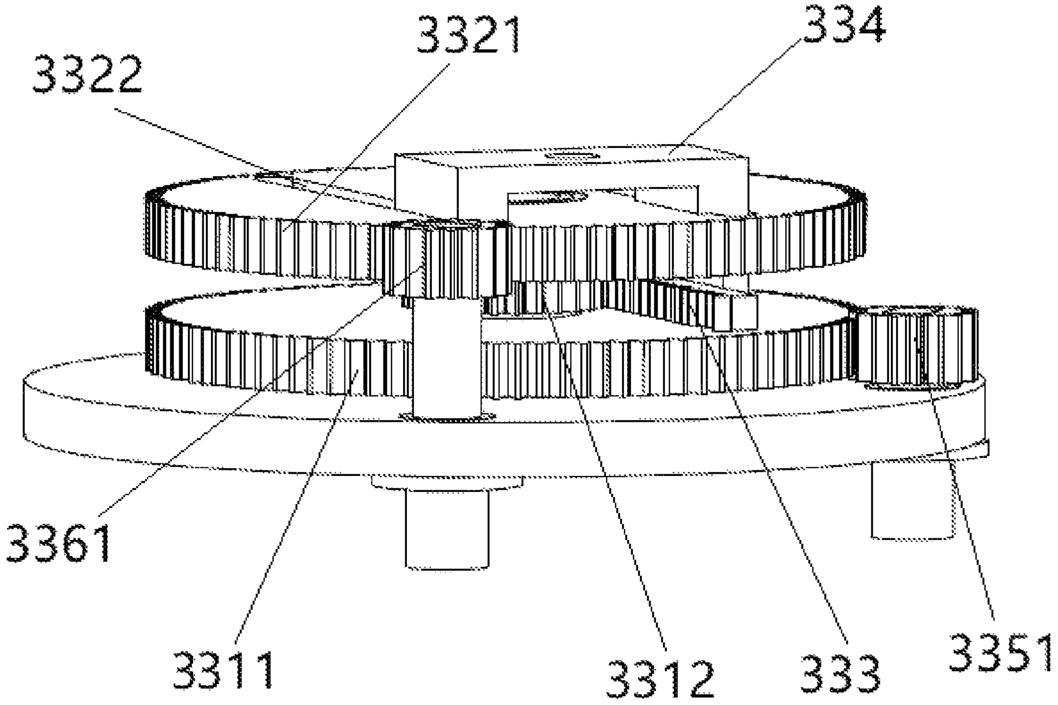
FIG. 17 shows a schematic structural diagram of the drive transmission mechanism shown in FIG. 15 according to some embodiments of the present disclosure.

FIGS. 15 and 16 respectively show a partial schematic structural diagram of a continuum instrument 10 (or 20, 30) according to some embodiments of the present disclosure including another drive transmission mechanism 330. FIG. 17 shows a schematic structural diagram of the drive transmission mechanism 330 according to some embodiments of the present disclosure. In some embodiments, as shown in FIGS. 16 and 17, the drive transmission mechanism 330 may include a gear and rack mechanism, which may include a first rotatable member 331, a second rotatable member 332, and a moving assembly. The first rotatable member 331 may be used for being driven by a first drive member 335 to rotate, the second rotatable member 332 is coaxially disposed with the first rotatable member 331 and may be used for being driven by a second drive member 336 to rotate relative to the first rotatable member 331, and the second rotatable member 332 is provided with a sliding guide portion 3322. At least a portion of the moving assembly is slidably disposed on the sliding guide portion 3322, at least another portion of the moving assembly is disposed to move linearly along with the rotation of the first rotatable member 331, and a distal end of the moving assembly is hinged to the input end of the drive connection part 120 (or 220, 320).

In some embodiments, as shown in FIGS. 16 and 17, the second rotatable member 332 may be arranged above the first rotatable member 331 in an overlapping manner, and the two rotatable members are rotatable relative to each other. As shown in FIGS. 16 and 17, in some embodiments, the first rotatable member 331 may include a meshing gear 3312 and a first driven gear 3311 coaxially and fixedly connected to each other, and the meshing gear 3312 is located at a distal side of the first driven gear 3311. The first drive member 335 may include a first driving gear 3351, the second rotatable member 332 may include, for example, a second driven gear 3321, and the second drive member 336 may include a second driving gear 3361. The first driving gear 3351 meshes with the first driven gear 3311, the second driving gear 3361 meshes with the first driven gear 3311, and the second driven gear 3321 is arranged above the meshing gear 3312 in an overlapping manner. The first driving gear 3351 may be driven by a drive electric motor to drive the first driven gear 3311 to rotate, the second driving gear 3361 may be driven by the drive electric motor to drive the second driven gear 3321 to rotate, and the first driven gear 3311 and the second driven gear 3321 are rotatable relative to each other. In some embodiments, the first rotatable member 331 may include the meshing gear 3312 and a first gear coaxially and fixedly connected to each other, the second rotatable member 332 may include a second gear, the first drive member 335 and the second drive member 336 may include a drive electric motor (or a motor), and the first gear and the second gear can be respectively driven by the drive electric motor to rotate relative to each other. In some embodiments, the transmission mode of the first rotatable member 331 and the second rotatable member 332 may also be other transmission modes, such as belt pulley transmission or sprocket transmission.

Figure 18:
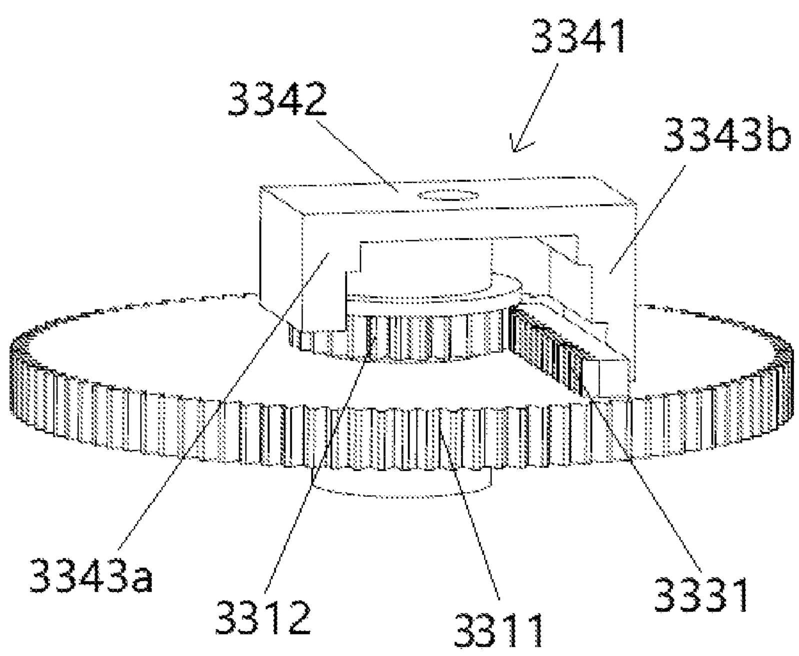
FIG. 18 shows a partial schematic structural diagram of the drive transmission mechanism shown in FIG. 15 according to some embodiments of the present disclosure.
Figure 19:
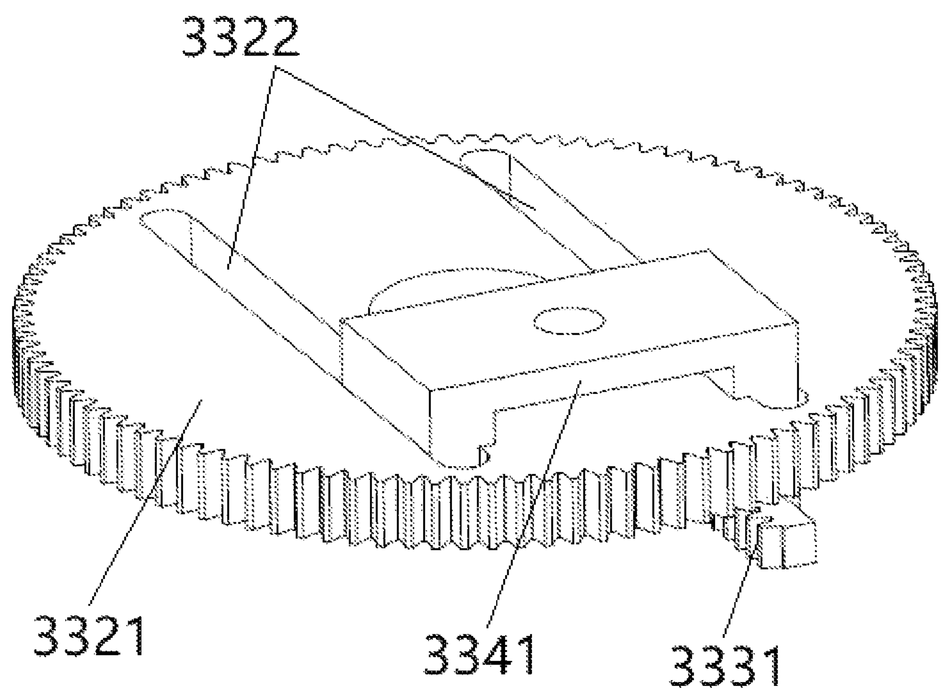
FIG. 19 shows a partial schematic structural diagram of the drive transmission mechanism shown in FIG. 15 according to some embodiments of the present disclosure.

As shown in FIGS. 16 and 17, in some embodiments, the moving assembly may include a sliding portion 334 and a meshing portion 333 which are fixedly connected to each other or integrally formed. The sliding portion 334 is slidably disposed on the sliding guide portion 3322 and is then guided by the sliding guide portion 3322 to slide linearly relative to the second rotatable member 332 (e.g., the second driven gear 3321), and the meshing portion 333 is disposed to mesh with the first rotatable member 331 (e.g., the first driven gear 3311) and then move linearly along with the rotation of the first rotatable member 331. FIGS. 18 and 19 show partial schematic structural diagrams of the drive transmission mechanism 330 according to some embodiments of the present disclosure. As shown in FIGS. 18 and 19, in some embodiments, the meshing portion 333 may include a rack 3331. The rack 3331 may mesh with the meshing gear 3312. It should be appreciated that the rack 3331 may be a spur rack, and the meshing gear 3312 may be a spur gear. In addition, the rack 3331 may also be a helical rack, and the meshing gear 3312 may also be a helical gear. In some embodiments, the sliding portion 334 may include a sliding block 3341, and the sliding guide portion 3322 may include at least one sliding groove provided in a direction parallel to the diameter of the second rotatable member 332, the sliding block 3341 is slidably disposed in the sliding groove, and one side of the sliding block 3341 passes through the sliding groove and is fixedly connected to the rack 3331. The rack 3331 may be driven by the meshing gear 3312 to move linearly so as to drive the sliding block 3341 to move along the sliding groove. In some embodiments, as shown in FIGS. 18 and 19, the sliding grooves may include a pair of sliding grooves symmetrically disposed along the diameter of the second rotatable member 332. The sliding block 3341 may include a sliding block body 3342 and sliding block side wings 3343*a* and 3343*b* proximally extending from two ends of the sliding block body 3342. Inner sides of the sliding block side wings 3343*a* and 3343*b* are provided with snap-fit steps for cooperation with the sliding grooves. The sliding block side wing 3343*b* passes through the sliding groove and is then fixedly connected to the rack 3331. The sliding block body 3342 is used for being connected to the input end of the drive connection part 120 (or 220, 320). It should be appreciated that the sliding guide portion 3322 may also include at least one sliding rail (or sliding rod) disposed in a direction parallel to the diameter of the second rotatable member 332, and the sliding block 3341 is slidably disposed on the sliding rail. For example, the sliding block 3341 and the sliding rail may be in a groove-type cooperation.

Thus, as shown in FIGS. 15-17, when the first driving gear 3351 drives the first driven gear 3311 located at the lower layer to rotate while the second driving gear 3361 located at the upper layer remains stationary, the meshing gear 3312 fixedly connected to the first driven gear 3311 is driven to rotate, the rack 3331 meshing with the meshing gear 3312 is then driven to move linearly, and the sliding block 3341 fixedly connected to the rack 3331 is driven by the rack 3331 to move in the sliding groove of the second driven gear 3321, so as to drive the input end of the drive connection part 120 (or 220, 320) to freely move in a horizontal plane. Since the proximal stop disk 1112 can be driven by the drive connection part 120 to turn, the proximal base disk 1111 and the proximal stop disk 1112 are out of alignment and have the axes no longer coincident. The proximal stop disk 1112 turns to push and pull the plurality of proximal structural backbones 1113 which have ends fixed to the proximal stop disk 1112, so that the proximal continuum 111 bends and then drive the distal continuum 112 to bend corresponding to (e.g., in the same direction, in an opposite direction, or angled with) the proximal continuum 111, so that the distal continuum 112 can bend in a space along a specific bending plane. In the case where the second driving gear 3361 drives the second driven gear 3321 to rotate so that the first driving gear 3351 drives the first driven gear 3311 to rotate, and the second driven gear 3321 and the first driven gear 3311 synchronously rotate in the same direction (e.g., at a same speed), the position of the sliding block 3341 on the second rotatable member 332 does not change, but the azimuth angle of the plane of rotation of the sliding block 3341 changes (e.g., the sliding block moves in a circular motion in the plane), so as to change the orientation of the bending plane of the input end of the drive connection part 120 (or 220, 320). After the proximal continuum 111 is bent, the push and pull action generated on the proximal structural backbones 1113 is transferred to the distal structural backbones 1123 and the distal continuum 112 by means of the structural backbone guide tube bundle 113, so as to achieve the bending of the distal continuum 112 in a space along different bending planes. The second driven gear 3321 and the first driven gear 3311 are driven cooperatively to adjust the degree of bending of the proximal continuum 111 along the specific bending plane and the bending thereof in different bending planes, so as to achieve the bending of the distal continuum 112 in the space in any direction.

In some embodiments, as shown in FIG. 5, the connection nodes of kinematic relationship among the drive connection part 320 (or 120, 220), the proximal continuum 111, and the drive transmission mechanism 130 (or 230, 330) may be included as follows: a first connection node A which may refer to the connection relationship between the proximal base disk 1111 and the drive connection part 320 (or 120, 220), a second connection node B which may refer to the distal structure of the drive connection part itself (e.g., a distal universal coupling joint, a distal spherical hinge joint or a distal hinge joint), a third connection node C which may refer to the connection relationship between the drive connection part 320 and the proximal stop disk 1112, a fourth connection node D which may refer to the proximal structure of the drive connection part 320 itself (e.g., a proximal universal coupling joint, a proximal spherical hinge joint or a proximal hinge joint), a fifth connection node E which may refer to the connection relationship between the distal structure and the proximal structure of the drive connection part itself, and a sixth connection node F which may refer to the connection relationship between the input end of the drive connection part 320 and the drive transmission mechanism 130. The above connection nodes may be combined in some of the following connection modes: a cylindrical pair (which may be rotatable or movable), a moving pair (which can move only), a rotating pair (which can rotate only), a fixed connection, and the structure of the drive connection part itself, so as to achieve the minimum degree of freedom required for driving the proximal continuum 111 to bend by means of combining the connection nodes.

In some embodiments, as shown in FIG. 7, when the drive transmission mechanism uses the planar drive transmission mechanism 130 (or 230, 330), a moving pair in the axial direction of the distal end of the drive connection part 120 may be provided between the distal end of the drive connection part 120 (or 220, 320) and the proximal base disk

1111, or a moving pair in the axial direction of the proximal end of the drive connection part 120 may be provided between the proximal end of the drive connection part 120 and the proximal stop disk 1112, or a moving pair in the axial direction of the distal end or the proximal end of the drive connection part 120 may be provided between the distal end or the proximal end thereof.

In some embodiments, as shown in FIGS. 1, 2(*b*) and 7, the drive transmission mechanism may be the drive transmission mechanism 130 (or 230, 330), and the drive connection part may be the drive connection part 120 (or 220, 320). The drive connection part 120 may include a distal universal coupling joint 121*a* and a proximal universal coupling joint 121*b*. In this case, the connection nodes may be combined as follows: the first connection node A is connected in a fixed manner, the second connection node B is connected by using the universal coupling 1211, the third connection node C is connected by using a cylindrical pair, the fourth connection node D is connected by using the universal coupling 1211', the fifth connection node E is connected by using a cylindrical pair, and the sixth connection node F is connected in a fixed manner. For example, the first connection node A may refer to the structure in which the link rod 1212*a* at the distal end of the universal coupling 1211 is fixedly connected to the proximal base disk 1111, the second connection node B may refer to the distal universal coupling 1211, the third connection node C may refer to the structure in which the outer circular surface of the link rod 1212*b* or 1212*a'* and the proximal stop disk 1112 cooperate with each other by means of the cylindrical pair, the fourth connection node D may refer to the proximal universal coupling 1211', the fifth connection node E may refer to the structure in which the link rod 1212*b* and the link rod 1212*a'* cooperate with each other by means of the cylindrical pair, and the sixth connection node F may refer to the structure in which the link rod 1212*b'* (as an input end of the drive connection part 120) at the proximal end of the universal coupling 1211' is fixedly connected to the drive transmission mechanism 130. The output shaft 136 of the drive transmission mechanism 130 drives the input end of the drive connection part 120 to freely move in a horizontal plane, and since the movement is allowed between the proximal universal coupling joint 121*b* and the distal universal coupling joint 121*a*, or between the distal universal coupling joint 121*a* and the proximal base disk 1111, or between the proximal universal coupling joint 121*b* and the proximal stop disk 1112, the distance between the input end of the drive connection part 120 and the proximal base disk 1111 in a vertical direction (the axial direction of the drive connection part 120 in an initial position) is substantially constant. When there is an included angle formed between the axial directions of the distal universal coupling joint 121*a* and the proximal universal coupling joint 121*b* and the vertical direction, the proximal stop disk 1112 can be driven to turn so as to achieve the bending of the proximal continuum 111, the plurality of proximal structural backbones 1113 which have ends fixed to the proximal stop disk 1112 are then pushed and pulled, so as to drive the distal continuum 112 to bend corresponding to (e.g., in an opposite direction with) the proximal continuum 111. Thus, the above connection nodes cooperate with each other, such that the proximal stop disk 1112 can slide up and down or turn relative to the drive connection part 120, or the drive connection part 120 can slide up and down or turn relative to the output shaft 136, so as to allow the proximal continuum 111 to generate a parasitic motion sliding in the axial direction (slipping up and down) and a bending motion in any direction (rotation) during bending. The parasitic motion may prevent the distal continuum 112 from generating an axial telescoping motion during bending that may cause wrinkling or excessive stretching of an envelope that covers the outer periphery of the distal continuum 112 to affect the service life of the cover.

In some embodiments, as shown in FIGS. 1, 2(*b*) and 7, the drive transmission mechanism may be the drive transmission mechanism 130 (or 230, 330), and the drive connection part may be the drive connection part 120 (or 220, 320). The connection nodes may be combined as follows: the first connection node A is connected in a fixed manner, the second connection node B is connected by using the universal coupling 1211, the third connection node C is connected by using a moving pair, the fourth connection node D is connected by using the universal coupling 1211', the fifth connection node E is connected by a moving pair, and the sixth connection node F is connected by using a rotating pair. In this way, it is also possible to allow the input end of the drive connection part 120 to be driven by the output shaft 136 to move in the horizontal plane, and the proximal stop disk 1112 is then driven to move and turn so as to achieve the bending of the distal continuum 112. In some embodiments, the connection nodes may also be combined as follows: the first connection node A is connected by using a moving pair, the second connection node B is connected by using the universal coupling 1211, the third connection node C is connected by using a moving pair, the fourth connection node D is connected by using the universal coupling 1211', the fifth connection node E is connected in a fixed manner, and the sixth connection node F is connected by using a rotating pair. In some embodiments, the universal coupling 1211 or 1211' may be replaced with a spherical hinge 2211. It should be appreciated that the connection nodes may also be combined in other forms of some of the above connection modes, such that under the premise of achieving a similar function (driving the proximal continuum 111 to bend), the more degrees of freedom, the more pliable and flexible the flexible continuum structure 110 will be.

In some embodiments, as shown in FIGS. 3, 4(*b*) and 12, the drive transmission mechanism may be the drive transmission mechanism 230 (or 130, 330), and the drive connection part may be the drive connection part 220 (or 120, 320). The drive connection part 220 may include at least one distal spherical hinge joint 221*a* and at least one proximal spherical hinge joint 221*b*. In this case, the connection nodes may be combined as follows: the first connection node A is connected in a fixed manner, the second connection node B is connected by using the spherical hinge 2211, the third connection node C is connected by using a cylindrical pair, the fourth connection node D is connected by using the spherical hinge 2211', the fifth connection node E is connected by using a cylindrical pair, and the sixth connection node F is connected in a fixed manner. For example, the first connection node A may refer to the structure in which the link rod 2212*a* at the distal end of the spherical hinge 2211 is fixedly connected to the proximal base disk 1111, the second connection node B may refer to the distal spherical hinge 2211, the third connection node C may refer to the structure in which the outer circular surface of the link rod 2212*b* or 2212*a'* and the proximal stop disk 1112 cooperate with each other by means of the cylindrical pair, the fourth connection node D may refer to the proximal spherical hinge 2211', the fifth connection node E may refer to the structure in which the link rod 2212*b* and the link rod 2212*a'* cooperate with each other by means of the cylindrical pair, and the sixth connection node F may refer to the structure in which the link rod 2212*b*' (as the input end of the drive connection part 220) at the proximal end of the spherical hinge 2211' is fixedly connected to the drive transmission mechanism 230. The sliding assembly 234 (e.g., the sliding pin 2341) of the drive transmission mechanism 230 drives the input end of the drive connection part 220 to freely move in a horizontal plane, and since the movement is allowed between the proximal spherical hinge joint 221*b* and the distal spherical hinge joint 221*a*, or between the distal spherical hinge joint 221*a* and the proximal base disk 1111, or between the proximal spherical hinge joint 221*b* and the proximal stop disk 1112, the distance between the input end of the drive connection part 220 and the proximal base disk 1111 in a vertical direction (the axial direction of the drive connection part 220 in an initial position) is substantially constant. When there is an included angle formed between the axial directions of the distal spherical hinge joint 221*a* and the proximal spherical hinge joint 221*b* and the vertical direction, the proximal stop disk 1112 can be driven to turn so as to achieve the bending of the proximal continuum 111, the plurality of proximal structural backbones 1113 which have ends fixed to the proximal stop disk 1112 are then pushed and pulled, so as to drive the distal continuum 112 to bend corresponding to (e.g., in an opposite direction with) the proximal continuum 111.

In some embodiments, as shown in FIGS. 3, 4(*b*) and 12, the drive transmission mechanism may be the drive transmission mechanism 230 (or 130, 330), and the drive connection part may be the drive connection part 220 (or 120, 320). The connection nodes may be combined as follows: the first connection node A is connected in a fixed manner, the second connection node B is connected by using the spherical hinge 2211, the third connection node C is connected by using a moving pair, the fourth connection node D is connected by using the spherical hinge 2211', the fifth connection node E is connected by a moving pair, and the sixth connection node F is connected by using a rotating pair. In this way, it is also possible to achieve that the input end of the drive connection part 220 can be driven by the sliding assembly 234 to move in the horizontal plane, and the proximal stop disk 1112 is then driven to move and turn so as to achieve the bending of the distal continuum 112. In this case, the connection nodes may also be combined as follows: the first connection node A is connected in a fixed manner, the second connection node B is connected by using the spherical hinge 2211, the third connection node C is connected by using a moving pair, the fourth connection node D is connected by using the spherical hinge 2211', the fifth connection node E is connected in a fixed manner, and the sixth connection node F is connected by using a rotating pair. In some embodiments, the spherical hinge 2211 or 2211' may be replaced with the universal coupling 1211. It should be appreciated that the connection nodes may also be combined in other forms of some of the above connection modes.

In some embodiments, as shown in FIGS. 5, 6 and 17, the drive transmission mechanism may be the drive transmission mechanism 330 (or 130, 230), and the drive connection part may be the drive connection part 320 (or 120, 220). The drive connection part 320 may include a hinge joint 321. The hinge joint 321 may include a distal link rod 3211*a*, a distal link rod 3211*b*, a proximal link rod 3212*a*, and a proximal link rod 3212*b*. The connection nodes may be combined as follows: the first connection node A is connected by using a rotating pair, the second connection node B is connected by using a rotating pair, the third connection node C is connected by using a cylindrical pair, the fourth connection node D is connected by using a rotating pair, the fifth connection node E is connected by using a cylindrical pair, and the sixth connection node F is connected in a fixed manner. For example, the first connection node A may refer to the structure in which the distal end of the distal link rod 3211*a* is connected to the proximal base disk 1111 by means of a rotating pair, the second connection node B may refer to the structure in which the proximal end of the distal link rod 3211*a* is hinged to the distal end of the distal link rod 3211*b*, the third connection node C may refer to the structure in which the outer circular surface of the distal link rod 3211*b* or the proximal link rod 3212*a* passes through the proximal stop disk 1112 to cooperate by means of a cylindrical pair, the fourth connection node D may refer to the structure in which the proximal end of the proximal link rod 3212*a* is hinged to the distal end of the proximal link rod 3212*b*, the fifth connection node E may refer to the structure in which the proximal end of the distal link rod 3211*b* cooperates with the distal end of the proximal link rod 3212*a* by means of a cylindrical pair, and the sixth connection node F may refer to the structure in which the proximal link rod 3212*b* (serving as the input end of the drive connection part 320) is fixedly connected to the drive transmission mechanism 330. The hinge axes X of the distal link rods 3211*a* and 3211*b* are perpendicular to the axial directions of the distal link rods 3211*a-b*, the hinge axes X' of the proximal link rods 3212*a* and 3212*b* are perpendicular to the axial directions of the proximal link rods 3212*a-b*, and the hinge axis X and the hinge axis X' are parallel to each other. The sliding portion 334 (e.g., the sliding block 3341) of the drive transmission mechanism 330 drives the input end of the drive connection part 220 to freely move in the horizontal plane, and since the movement is allowed between the distal link rod 3211*b* and the proximal link rod 3212*a* (or between the distal link rod 3211*a* and the proximal base disk 1111, or between the distal link rod 3211*b* or the proximal link rod 3212*a* and the proximal stop disk 1112), the distance between the input end of the drive connection part 320 and the proximal base disk 1111 in the vertical direction (the axial direction of the drive connection part 320 in an extended position) is substantially constant. When there is an included angle formed between the axial directions of the distal link rods 3211*a-b* and the proximal link rods 3212*a-b* and the vertical direction, the proximal stop disk 1112 can be driven to turn so as to achieve the bending of the proximal continuum 111, the plurality of proximal structural backbones 1113 which have ends fixed to the proximal stop disk 1112 are then pushed and pulled, so as to drive the distal continuum 112 to bend corresponding to (e.g., in an opposite direction with) the proximal continuum 111.

In some embodiments, as shown in FIGS. 5, 6 and 17, the drive transmission mechanism may be the drive transmission mechanism 330 (or 130, 230), and the drive connection part may be the drive connection part 320 (or 120, 220). The connection nodes may be combined as follows: the first connection node A is connected by using a rotating pair, the second connection node B is connected by using a rotating pair, the third connection node C is connected by using a cylindrical pair, the fourth connection node D is connected by using a rotating pair, the fifth connection node E is connected by using a cylindrical pair, and the sixth connection node F is connected by using a rotating pair. It should be appreciated that the connection nodes may also be combined in other forms of some of the above connection modes.

As shown in FIG. 1, in some embodiments, the proximal continuum 111 may further include at least one proximal retaining disk 1114 disposed between the proximal base disk 1111 and the proximal stop disk 1112, and the plurality of proximal structural backbones 1113 sequentially pass through the at least one proximal retaining disk 1114. As shown in FIG. 1, in some embodiments, the distal continuum 112 may further include at least one distal retaining disk 1124 disposed between the distal base disk 1121 and the distal stop disk 1122, and the plurality of distal structural backbones 1123 also pass through the at least one distal retaining disk 1124 in sequence. The proximal retaining disk 1114 and the distal retaining disk 1124 are used for respectively supporting the structural backbones in the radial directions of the proximal structural backbones 1113 and the distal structural backbones 1123, such that the proximal structural backbones 1113 and the distal structural backbones 1123 remain in a parallel state during the bending transformation, which can prevent the proximal structural backbones 1113 and the distal structural backbones 1123 from destabilizing during the bending motion. In some embodiments, at least one tube bundle retaining disk 1131 is disposed on the structural backbone guide tube bundle 113, as shown in FIG. 7, a proximal end of the structural backbone guide tube bundle 113 is fixedly connected to the proximal base disk 1111, and a distal end of the structural backbone guide tube bundle 113 passes through the at least one tube bundle retaining disk 1131 and is then fixedly connected to the distal base disk 1121.

In some embodiments, the proximal structural backbone 1113 and the distal structural backbone 1123 may include elastic wires or tubes made of a hyperelastic material, for example, may be made of an elastic metallic material having high strength and high toughness, such as a nickel-titanium alloy. The structural backbone guide tube bundle 113 may include a plurality of thin tubes made of a steel material to form a steel tube bundle.

In some embodiments, the continuum instrument 40 may include at least two continuum instruments 10 (or 20, 30) in the embodiments described above. In some embodiments, the continuum instrument 40 includes at least two continuum instruments 10 (or 20, 30) connected in series or in parallel.

Figure 20:
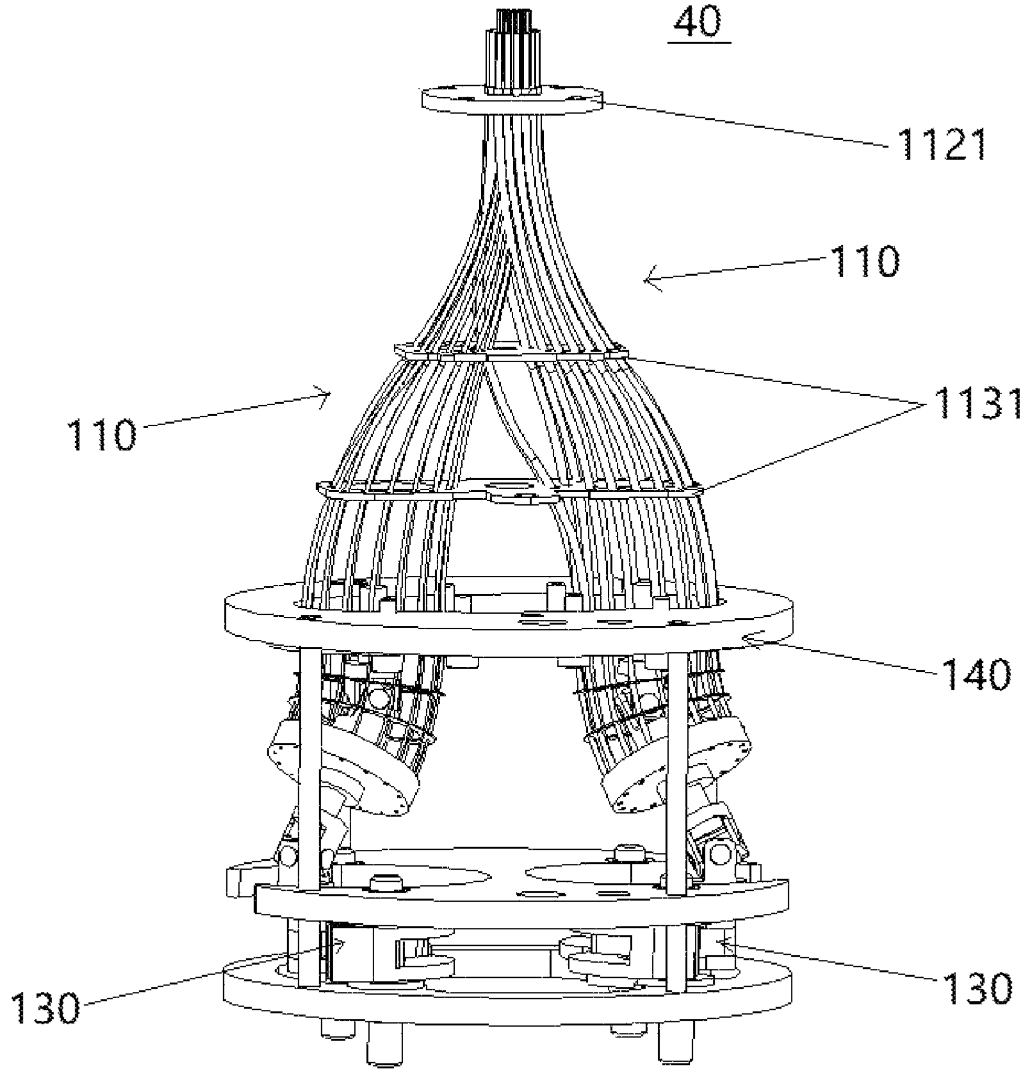
FIG. 20 shows a partial schematic structural diagram of another continuum instrument according to some embodiments of the present disclosure.

FIG. 20 shows a partial schematic structural diagram of the continuum instrument 40 according to some embodiments of the present disclosure. As shown in FIG. 20, in some embodiments, the continuum instrument 40 further includes a support 140. The proximal base disks 1111 of the at least two flexible continuum structures 110 are respectively fixedly connected to or integrally formed with the support 140, the proximal ends of the at least two structural backbone guide tube bundles 113 are respectively fixedly connected to the proximal base disks 1111 of the proximal continua 111, and the distal ends of the at least two structural backbone guide tube bundles 113 respectively pass through the support 140 in sequence and converge into one bundle at the distal base disk 1121. For example, the distal ends of the two structural backbone guide tube bundles 113 are distributed at the distal base disk 1121 along the circumference as one bundle or distributed within the circle. It should be appreciated that the distal ends of the two structural backbone guide tube bundles 113 may also be distributed at the distal base disk 1121 along the rectangular periphery as one bundle or distributed within the rectangle. In some embodiments, the proximal base disk 1111 or the distal base disk 1121 may directly form part of the support 140. In some embodiments, as shown in FIG. 20, at least two drive transmission mechanisms 130 (or 230, 330) are arranged side by side on the support 140, with an output end of each drive transmission mechanism 130 being respectively connected to the input end of at least one drive connection part 120 (or 220, 320). The at least two drive transmission mechanisms 130 respectively drive the proximal stop disks 1112 of the at least two flexible continuum structures 110 by means of the at least two input ends to turn, so that the proximal structural backbones 1113 of the at least two flexible continuum structures 110 are pushed and pulled so as to achieve the bending of at least two distal continua 112 in a space in different directions.

In some embodiments, the distal continua 112 in the at least two flexible continuum structures 110 of the continuum instrument 40 may have the same or different lengths. It will be appreciated that the distal ends of at least two structural backbone guide tube bundles 113 are converged at the distal base disk 1121. At least two distal continua 112 may be connected in series. For example, the proximal end of the first distal continuum distally extends from the distal base disk 1121 and is fixedly connected to the distal stop disk 1122, the distal base disk of the second distal continuum is connected to or is the same as the distal stop disk 1122 of the first distal continuum, and the distal end of the second distal continuum may be fixedly connected to the distal stop disk 1122. Thus, the at least two drive transmission mechanisms 130 (or 230, 330) respectively drive the at least two drive connection parts 120 (or 220, 320) to move to respectively drive the at least two proximal continua 111 to move, so that the distal continua 112 bends so as to increase the degree of freedom of the distal continua 112 and thus improve the flexibility of the continuum instrument.

Figure 21:
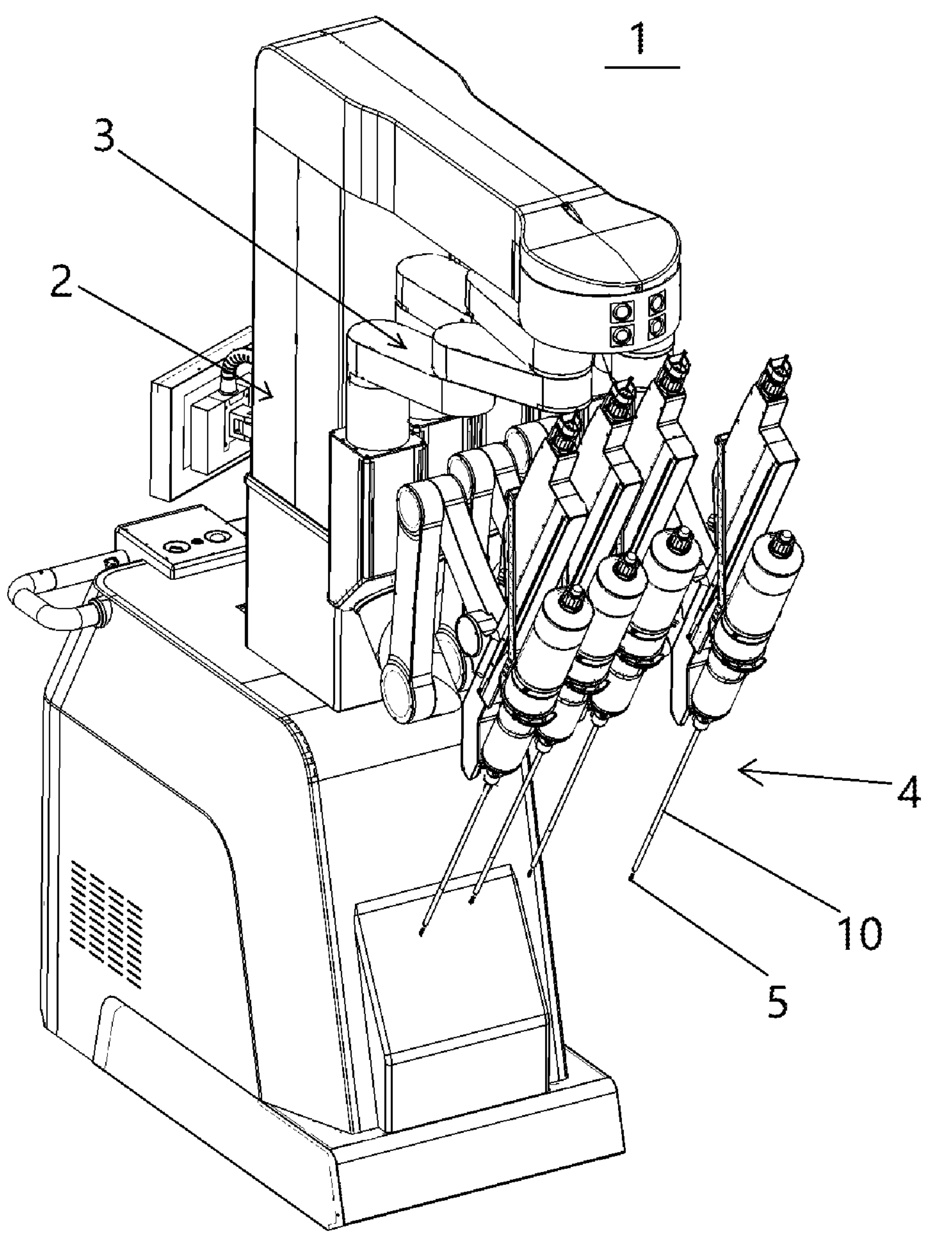
FIG. 21 shows a partial schematic structural diagram of a surgical robot according to some embodiments of the present disclosure.

In some embodiments, the present disclosure further provides a surgical robot. The surgical robot includes at least one continuum instrument 10 (or 20, 30, 40) in the embodiments described above. FIG. 21 shows a schematic structural diagram of a surgical robot 1 according to some embodiments of the present disclosure. As shown in FIG. 21, in some embodiments, the surgical robot 1 may further include at least one surgical trolley 2, at least one positioning arm 3, and at least one surgical instrument 4. At least one positioning arm 3 is movably disposed on the at least one surgical trolley 2, and at least one surgical instrument 4 is disposed at the distal end of the at least one positioning arm 3. The surgical instrument 4 includes the continuum instrument 10 (or the continuum instrument 20, 30, or 40) and an end device 5 disposed at the distal end of the continuum instrument 10. It should be appreciated that the end device 5 may include a surgical end effector or an endoscope. The position of the continuum instrument may be adjusted by means of adjusting the positioning arm 3, and the posture of the end device 5 may be adjusted by means of the continuum instrument. The continuum instrument is compact in structure and has high reliability and flexibility, and can improve the safety of the surgical robot.

It should be noted that the foregoing description merely includes exemplary embodiments of the present disclosure and the technical principles applied. It will be appreciated by those skilled in the art that the present disclosure is not limited to the particular embodiments herein, and various obvious changes, readjustments and substitutions can be made by those skilled in the art without departing from the scope of protection of the present disclosure. Therefore, although the present disclosure has been described in detail with reference to the above embodiments, the present disclosure is not limited merely to the above embodiments, and can also include more other equivalent embodiments without departing from the concept of the present disclosure, and the scope of protection of the present disclosure is determined by the scope of the appended claims.

The invention claimed is:

1. A continuum instrument, comprising:

at least one proximal continuum comprising a proximal stop disk, a proximal base disk and a plurality of proximal structural backbones, proximal ends of the plurality of proximal structural backbones passing through the proximal base disk and being fixedly connected to the proximal stop disk;

at least one distal continuum comprising a distal stop disk and a plurality of distal structural backbones, distal ends of the plurality of distal structural backbones being fixedly connected to the distal stop disk, and the plurality of distal structural backbones being fixedly connected to or integrally formed with the plurality of proximal structural backbones;

a drive connection part comprising a distal drive connection structure located at a distal side of the proximal stop disk and a proximal drive connection structure located at a proximal side of the proximal stop disk, a distal end of the distal drive connection structure being connected to the proximal base disk, a proximal end of the distal drive connection structure being connected to a distal end of the proximal drive connection structure to form a rod-shaped connection node; the rod-shaped connection node passing through the proximal stop disk, being located inside and on both side of the proximal stop disk, and being movably connected to the proximal stop disk to form a cylindrical pair or a moving pair; and a drive transmission mechanism located outside the proximal continuum, an output end of the drive transmission mechanism being connected to a proximal end of the proximal drive connection structure located at the proximal side of the proximal stop disk to output a single planar motion, the output end of the drive transmission mechanism being configured to drive the rod-shaped connection node to move by means of the proximal drive connection structure so as to turn the proximal stop disk by means of the cylindrical pair or the moving pair, thereby driving the distal continuum to bend by means of the proximal structural backbones and the distal structural backbones.

2. The continuum instrument according to claim 1, wherein the proximal drive connection structure of the drive connection part comprises at least one proximal universal coupling joint or proximal spherical hinge joint, the distal drive connection structure of the drive connection part comprises at least one distal universal coupling joint or distal spherical hinge joint, a distal link rod of the distal universal coupling joint or distal spherical hinge joint being connected to the proximal base disk, a proximal link rod of the distal universal coupling joint or distal spherical hinge joint being connected to a distal link rod of the proximal universal coupling joint or proximal spherical hinge joint to form the rod-shaped connection node, a proximal link rod of the proximal universal coupling joint or proximal spherical hinge joint being connected to the output end of the drive transmission mechanism to receive the single planar motion; or the distal drive connection structure of the drive connection part comprises at least one distal hinge joint comprising a first link rod and a second link rod hingedly connected to each other, the proximal drive connection structure of the drive connection part comprises at least one proximal hinge joint comprising a third link rod and a fourth link rod hingedly connected to each other, a distal end of the first link rod being connected to the proximal base disk, a proximal end of the second link rod being connected to a distal end of the third link rod to form the rod-shaped connection node, a proximal end of the fourth link rod being connected to the output end of the drive transmission mechanism to receive the single planar motion.

3. The continuum instrument according to claim 1, wherein the drive transmission mechanism comprises a planar link mechanism, which comprises a first connecting rod, a second connecting rod, a third connecting rod, a fourth connecting rod, a fifth connecting rod, a first input shaft, and a second input shaft; and the first connecting rod is fixedly disposed, and the first input shaft and the second input shaft are rotatably disposed on the first connecting rod; one end of the second connecting rod is fixedly connected to the first input shaft, and the other end of the second connecting rod is hinged to one end of the third connecting rod; one end of the fifth connecting rod is fixedly connected to the second input shaft, and the other end of the fifth connecting rod is hinged to one end of the fourth connecting rod; the other end of the fourth connecting rod is hinged to the other end of the third connecting rod, and the other end of the third connecting rod and the other end of the fourth connecting rod are connected to the input end of the drive connection part.

4. The continuum instrument according to claim 1, wherein the drive transmission mechanism comprises a gear and sliding groove mechanism, which comprises:

a first rotatable member configured to be driven by a first drive member to rotate;

a moving member configured to be driven by the first rotatable member to rotate, with the center of rotation of the moving member being offset from the center of rotation of the first rotatable member, the moving member being provided with a first sliding guide portion;

a second rotatable member coaxially disposed with the first rotatable member and configured to be driven by a second drive member to rotate relative to the first rotatable member, the second rotatable member being provided with a second sliding guide portion; and a sliding assembly slidably connected to the first sliding guide portion and the second sliding guide portion to slide along the first sliding guide portion and the second sliding guide portion, the sliding assembly being connected to the input end of the drive connection part.

5. The continuum instrument according to claim 4, wherein the moving member comprises a meshing portion configured to mesh with the first rotatable member.

6. The continuum instrument according to claim 5, wherein an inner peripheral surface of the first rotatable member is provided with inner ring teeth, the meshing portion comprises teeth disposed on an outer peripheral surface of the moving member, and the teeth on the outer peripheral surface of the moving member mesh with the inner ring teeth of the first rotatable member to drive the moving member to rotate with the first rotatable member.

7. The continuum instrument according to claim 6, wherein the gear and sliding groove mechanism further comprises a rotating shaft, which has a proximal end fixedly connected to the moving member and a distal end rotatably connected to the second rotatable member.

8. The continuum instrument according to claim 4, wherein the first sliding guide portion is a first sliding groove, and the second sliding guide portion is a second sliding groove extending in a direction perpendicular to the axis of rotation of the second rotatable member; and the sliding assembly comprises a sliding pin movably disposed the first sliding groove and the second sliding groove in a penetrating manner, with a distal end of the sliding pin being connected to the input end of the drive connection part.

9. The continuum instrument according to claim 8, wherein the sliding assembly further comprises a sliding block fixedly connected to the sliding pin, the second rotatable member is provided with a sliding rail parallel to the second sliding groove, and the sliding block is slidably disposed on the sliding rail.

10. The continuum instrument according to claim 4, wherein the first sliding guide portion is a first sliding rail, and the second sliding guide portion is a second sliding rail; and the sliding assembly comprises a first sliding block, a second sliding block and a sliding pin, the first sliding block being slidably disposed on the first sliding rail, the second sliding block being slidably disposed on the second sliding rail, one of the first sliding block and the second sliding block being disposed to be movably connected to the sliding pin, and the other of the first sliding block and the second sliding block being disposed to be fixedly connected to the sliding pin.

11. The continuum instrument according to claim 1, wherein the drive transmission mechanism comprises a gear and rack mechanism, which comprises:

a first rotatable member configured to be driven by a first drive member to rotate;

a second rotatable member coaxially disposed with the first rotatable member and configured to be driven by a second drive member to rotate relative to the first rotatable member, the second rotatable member being provided with a sliding guide portion; and a moving assembly, at least a portion of the moving assembly being slidably disposed on the sliding guide portion, at least another portion of the moving assembly being disposed to move linearly along with the rotation of the first rotatable member, and a distal end of the moving assembly being connected to the input end of the drive connection part.

12. The continuum instrument according to claim 11, wherein the moving assembly comprises a sliding portion and a meshing portion connected to each other, the sliding portion being slidably disposed on the sliding guide portion and guided by the sliding guide portion to slide linearly relative to the second rotatable member, and the meshing portion being disposed to mesh with the first rotatable member so as to move linearly along with the rotation of the first rotatable member.

13. The continuum instrument according to claim 12, wherein the first rotatable member comprises a meshing gear and a first driven gear coaxially and fixedly connected to each other, the meshing gear being located at a distal side of the first driven gear; and the meshing portion comprises a rack which meshes with the meshing gear.

14. The continuum instrument according to claim 13, wherein the sliding portion comprises a sliding block, the rack is disposed at a proximal end of the sliding block, the sliding guide portion comprises a sliding groove provided in the second rotatable member, the sliding block is slidably disposed in the sliding groove, the proximal end of the sliding block passes through the sliding groove and is then fixedly connected to the rack, and the sliding block is movably connected to the proximal stop disk to enable the sliding block and the proximal stop disk to slide and/or rotate relative to an axial direction of the proximal stop disk.

15. The continuum instrument according to claim 1, wherein the distal continuum further comprises a distal base disk through which the plurality of distal structural backbones pass; the continuum instrument further comprises a structural backbone guide tube bundle connected between the proximal base disk and the distal base disk; and the plurality of proximal structural backbones or the plurality of distal structural backbones pass through the proximal base disk and the structural backbone guide tube bundle.

16. The continuum instrument according to claim 15, comprising at least two proximal continua, at least two distal continua, at least two structural backbone guide tube bundles, at least two drive connection parts, and at least two drive transmission mechanisms, wherein the at least two proximal continua are connected in series or in parallel.

17. The continuum instrument according to claim 16, further comprising a support, wherein the proximal base disks of the at least two proximal continua are respectively fixedly connected to or integrally formed with the support, the proximal ends of the at least two structural backbone guide tube bundles are respectively fixedly connected to the proximal base disks of the proximal continua, and the distal ends of the at least two structural backbone guide tube bundles pass through the support and converge into one bundle at the distal base disk; and the at least two drive transmission mechanisms are arranged side by side on the support, and the output end of each of the drive transmission mechanisms is connected to the input end of corresponding drive connection part to drive the proximal stop disk of the proximal continuum to turn, so as to drive the corresponding distal continuum to bend.

18. A surgical robot, comprising at least one surgical trolley, at least one positioning arm, and at least one surgical instrument, wherein the at least one surgical instrument comprises at least one continuum instrument according to claim 1 and an end device disposed at a distal end of the continuum instrument; and the at least one positioning arm is movably disposed on the at least one surgical trolley, and the at least one surgical instrument is disposed at a distal end of the at least one positioning arm.

* * * * *